US009737559B2

(12) United States Patent
Gorgani

(10) Patent No.: US 9,737,559 B2
(45) Date of Patent: Aug. 22, 2017

(54) SYNERGISTIC ANTI-DIABETIC COMPOSITIONS

(71) Applicant: Ozstar Therapeutics Pty Ltd, Beaumont Hills, New South Wales (AU)

(72) Inventor: Nick Naser Gorgani, Beaumont Hills (AU)

(73) Assignee: Ozstar Therapeutics Pty Ltd, Waverton, New South Wales (AU)

( * ) Notice: Subject to any disclaimer, the term of this patent is extended or adjusted under 35 U.S.C. 154(b) by 163 days.

(21) Appl. No.: 14/359,759

(22) PCT Filed: Nov. 23, 2012

(86) PCT No.: PCT/AU2012/001442
§ 371 (c)(1),
(2) Date: May 21, 2014

(87) PCT Pub. No.: WO2013/075172
PCT Pub. Date: May 30, 2013

(65) Prior Publication Data
US 2014/0303118 A1 Oct. 9, 2014

(30) Foreign Application Priority Data

Nov. 23, 2011 (AU) ................................ 2011904887
Jun. 27, 2012 (AU) ................................ 2012902723

(51) Int. Cl.
*A61K 31/733* (2006.01)
*A61K 31/64* (2006.01)
(Continued)

(52) U.S. Cl.
CPC .......... *A61K 31/733* (2013.01); *A61K 31/635* (2013.01); *A61K 31/64* (2013.01); *A61K 45/06* (2013.01)

(58) Field of Classification Search
None
See application file for complete search history.

(56) References Cited

U.S. PATENT DOCUMENTS 4,082,842 A * 4/1978 Nahle .................. A61K 31/635
514/157
5,972,973 A 10/1999 Whitcomb .................... 514/342
(Continued)

FOREIGN PATENT DOCUMENTS

CN         1861173 A  * 11/2006  .......... A61K 36/899
JP       2008-500955      1/2008  .......... A61K 31/198
(Continued)

OTHER PUBLICATIONS

Wang et al., CN 1861173 A, Nov. 2006, machine translation, Retreived on Mar. 15, 2016 from http://worldwide.espacenet.com.*
(Continued)

*Primary Examiner* — Shaojia Anna Jiang
*Assistant Examiner* — Dale R Miller
(74) *Attorney, Agent, or Firm* — Sunstein Kann Murphy & Timbers LLP

(57) ABSTRACT

The present invention is concerned with improved synergistic compositions effective in the treatment of diabetes and/or hyperglycemia. In particular, the present invention is concerned with synergistic compositions comprising inulin preparations having a defined degree of polymerisation (DP) of below about 25 and sulfonylureas and/or a sulfonamide and/or derivatives and/or metabolites thereof used in the treatment of Type-2 Diabetes Meliitus (T2DM). Said compositions are also used for preventing the development of, or ameliorating, side-effects or conditions in a subject treated with sulfonylurea and/or a sulfonamide compounds (and/or derivatives and/or metabolites thereof, or combinations
(Continued)

thereof), said side-effects including hypoglycemia, gastrointestinal disturbances, fatigue, weight gain, and satiety.

29 Claims, 13 Drawing Sheets

(51) Int. Cl.
A61K 45/06 (2006.01)
A61K 31/635 (2006.01)

(56) References Cited

U.S. PATENT DOCUMENTS

| | | | | |
|---|---|---|---|---|
| 2003/0077335 | A1* | 4/2003 | Richardson | A61K 31/198 424/682 |
| 2003/0130205 | A1 | 7/2003 | Christian | 514/23 |
| 2007/0004623 | A1 | 1/2007 | Bellini et al. | 514/12 |
| 2009/0214511 | A1 | 8/2009 | Tran et al. | 424/94.61 |

FOREIGN PATENT DOCUMENTS

| | | | | |
|---|---|---|---|---|
| WO | WO 2006/138705 | 12/2006 | | A23P 1/08 |
| WO | WO 2008/138805 | 11/2008 | | A61K 8/06 |
| WO | WO 2010/122357 | 10/2010 | | A61K 47/36 |
| WO | WO 2010/124387 | 11/2010 | | A61K 35/74 |
| WO | WO 2011/146981 | 12/2011 | | A61K 31/733 |

OTHER PUBLICATIONS

Prophylactic. (2008). In Webster's new world™ medical dictionary. Retrieved from http://http://search.credoreference.com/content/entry/webstermed/prophylactic_1/0?searchId=33985857-eacf-11e5-8efa-0e811e6e1ce7&result=1.*
Delzenne, N. M., Cani, P. D., Daubioul, C., & Neyrinck, A. M. (2005). Impact of inulin and oligofructose on gastrointestinal peptides. British Journal of Nutrition, 93(S1), S157-S161.*
Cani, P. D., Dewever, C., & Delzenne, N. M. (2004). Inulin-type fructans modulate gastrointestinal peptides involved in appetite regulation (glucagon-like peptide-1 and ghrelin) in rats. British Journal of Nutrition, 92(3), 521-526.*
"Prevention" in Glossary of medical education terms: Parts 1-7. Wojtczak, A., Ed. Medical Teacher. vol. 24, No. 2-6 and vol. 25, No. 1&2. 2002.*
Rendell, M. (2004). The role of sulphonylureas in the management of type 2 diabetes mellitus. Drugs, 64(12), 1339-1358.*
Karunakara, S., Hammersley, M. S., Morris, R. J., Turner, R. C., Holman, R. R., & Fasting Hyperglycaemia Study Group. (1997). The Fasting Hyperglycaemia Study: III. Randomized controlled trial of sulfonylurea therapy in subjects with increased but not diabetic fasting plasma glucose. Metabolism, 46, 56-60.*
Wilkinson, G. Pharmacokinetics, The Dynamics of Drug Absorption, Distribution, and Elimination (2001). In: Goodman and Gilman's the pharmacological basis of therapeutics. International edition, 10th edition, Mc Grow Hill, 971.*
International Searching Authority, International Search Report—International Application No. PCT/AU2012/001442, dated Jan. 31, 2013, together with the Written Opinion of the International Searching Authority, 15 pages.
Franck et al., Active Food Scientific Monitor, an Orafti Newsletter, No. 12, 20 pages, Spring 2005.
Orafti, Orafti'S Beneo(TM)P95 Shown to Promote Satiety and to Limit Energy Intake in Humans, Orafti, http://newhope360.com/supply-news-amp-analysis/orafti-s-beneotmp95-shown-promote-satiety-and-limit-energy-intake-humans, 4 pages, May 22, 2015.
Bonsu et al., "Can dietary fructans lower serum glucose?" Journal of Diabetes, vol. 3, pp. 58-66, 2011.
DeFronzo, et al., "Pathophysiologic Approach to Therapy in Patients With Newly Diagnosed Type 2 Diabetes," Diabetes Care, vol. 36, Supp. 2, pp. S127-S138, Aug. 2013.
Perrin et al., "Oligofructose does not affect the development of type 1 diabetes mellitus induced by dietary proteins in the diabetes-prone BB rat model," Diabetes Nutr Metab., vol. 16, No. 2, pp. 94-101, Apr. 2003, Abstract.
Rozan et al., "Effects of lifelong intervention with an oligofructose-enriched inulin in rats on general health and lifespan," British Journal of Nutrition, vol. 100, pp. 1192-1199, 2008.
Mashkovsky, M.D., Drugs, Manual for Physicians, vol. 1, 14$^{th}$ revised, corrected and enlarged edition, Moscow, OOO "New Wave", editor S. D. Divov, 2 pages, 2001—(In Russian).
Mashkovsky, M.D., Drugs, Manual for Physicians, vol. 1, 14$^{th}$ revised, corrected and enlarged edition, Moscow, OOO "New Wave", editor S. D. Divov, 2 pages, 2001—(English translation).
Alles, M., et al., "Consumption of Fructooligosaccharides Does Not Favorably Affect Blood Glucose and Serum Lipid Concentrations in Patients with Type 2 Diabetes [1-3]," Am. J. Clin. Nutr., vol. 69, pp. 64-69 (1999).
Cani, P., et al., "Involvement of Endogenous Glucagon-like Peptide-1 (7-36) amide on Glycaemia-Lowering Effect of Oligofructose in Streptozotocin-Treated Rats," Journal of Endocrinology, vol. 185, pp. 457-465 (2005).
Causey, J., et al., "Effects of Dietary Inulin on Serum Lipids, Blood Glucose and the Gastrointestinal Environment in Hypercholesterolemic Men," Nutrition Research, vol. 20, No. 2, pp. 191-201 (2000).
Forcheron, F., et al., "Long-Term Administration of Inulin-Type Fructans has No Significant Lipid-Lowering Effect in Normolipidemic Humans," Metabolism Clinical and Experimental, vol. 56, pp. 1093-1098 (2007).
Giacco, R, et al., "Effects of Short-Chain Fructo-Oligosaccharides on Glucose and Lipid Metabolism in Mild Hypercholesterolaemic Individuals," Clinical Nutrition, vol. 23, pp. 331-340 (2004).
Klaus, N., "Routes of Administration," The Laboratory Rat (A Volume in Handbook of Experimental Animals), Chapter 24, pp. 463-482 (2000).
Letexier, D., et al., "Addition of Inulin to a Moderately High-Carbohydrate Diet Reduces Hepatic Lipogenesis and Plasma Triacyglycerol Concentrations in Human [1-3]," The American Journal of Clinical Nutrition, vol. 77, pp. 559-64 (2003).
Luo, J., et al. "Chronic Consumption of Short-Chain Fructooligosaccharides by Healthy Subjects Decreased Basal Hepatic Glucose Production but had no Effect on Insulin-Stimulated Glucose Metabolism [1-3]," Am. J. Clin. Nutr., vol. 63, pp. 939-45 (1996).
Luo, J., et al., "Chronic Consumption of Short-Chain Fructooligosaccharides Does Not Affect Basel Hepatic Glucose Production or Insulin Resistance in Type 2 Diabetics [1]," The American Society of Nutritional Sciences, vol. 130, No. 6, pp. 1572-1577 (2000).
Nugent, D, et al., "A Review of Islet of Langerhans Degeneration in Rodent Models of Type 2 Diabetes," Toxicologic Pathology, vol. 36, pp. 529-551 (2008).
Rehman, A., et al., "Drug-Induced Glucose Alterations Part 2: Drug-Induced Hyperglycemia," Diabetes Spectrum, vol. 24, No. 4, pp. 234-238 (2011).
Schaafsma, G. et al., "Effects of a Milk Product, Fermented by Lactobacillus Acidophilus and with Fructo-Oligosaccharides Added, on Blood Lipids in Male Volunteers," Eur. J. Clin. Nutr., vol. 52, No. 6, pp. 436-440 (1998) Abstract.
van Dokkum, et al., "Effect of Nondigestible Oligosaccharides on Large-Bowel Functions, Blood Lipid Concentrations and Glucose Absorption in Young Healthy Male Subjects," Eur. J. Clin. Nutr., vol. 53, No. 1, pp. 1-7 (1999) Abstract.
Verhoef, S., et al., "Effects of Oligofructose on Appetite Profile, Glucagon-Like Peptide 1 and Peptide YY3-36 Concentrations and Energy Intake," British Journal of Nutrition, vol. 106, No. 11, pp. 1757-62 (2011).

* cited by examiner

OFP MANUFACTURING PROCESS

Pre-treatment

- CHICORY ROOTS
- WASHING
- SLICING
- EXTRACTION

Purification

- PURIFICATION
- DEMINERALIZATION / DECOLORIZATION
- ACTIVATED CARBON
- MICROFILTRATION
- CONCENTRATION

Product

- PARTIAL HYDROLYSIS
- SPRAY DRYING
- PACKAGING
- SENSUS-OFP

FIGURE 13

SYNERGISTIC ANTI-DIABETIC COMPOSITIONS

TECHNICAL FIELD

The present invention is concerned with improved synergistic compositions effective in the treatment of diabetes and/or hyperglycemia. In particular, the present invention is concerned with synergistic compositions comprising inulin preparations with defined degree of polymerisation (DP) characteristics and sulfonylureas and/or sulphonamides and their derivatives and/or metabolites thereof, used in the treatment of Type-2 Diabetes Mellitus (T2DM).

BACKGROUND OF THE INVENTION

Any discussion of the prior art throughout the specification should in no way be considered as an admission that such prior art is widely known or forms part of common general knowledge in the field.

Previous studies, described in PCT/AU2011/000622, demonstrated for the first time that combination of inulin and sulfonylureas acted synergistically in inter alia lowering fasting blood glucose (FBG) levels in patients with Type-2 Diabetes Mellitus (T2DM). Synergy appeared to be restricted to sulfonylurea-class of compounds rather than—other examined anti-diabetic treatment in this study.

Preparations of inulin can be heterogeneous and can vary significantly with respect to the degree of polymerization (DP). Starting with natural sources, inulin will have a different DP range depending on the source (eg. DP in the range as low as 2 to about 60 for different natural sources). Inulins with DP in the range from 2 to about 10 are also referred to as fructo-oligosaccharides (FOS) and oligofructose (OF). Extraction and processing of inulin from natural sources will further contribute to this variation in DP as well as broadening the DP range and/or bias the range towards lower DP values. None of the earlier published studies provide any indication about the useful DP range for inulin and how this parameter may influence synergy with sulfonylureas in the treatment of T2DM.

There is therefore a need for better defined and improved synergistic inulin-sulfonylurea compositions, with more efficacious and predictable blood glucose level control, and improved dosing regimes.

It is an objective of the present invention to overcome or ameliorate at least one of the disadvantages of the prior art treatments, or to provide a useful alternative.

SUMMARY OF THE INVENTION

According to a first aspect the present invention provides improved synergistic composition comprising inulin having Degree of Polymerization (DP) below about 25 and a sulfonylurea and/or a sulfonamide and/or derivatives and/or metabolites thereof, or combinations thereof, for the treatment of diabetes.

Derivatives or metabolites of sulfonylureas, wherein such derivatives/metabolites have an active effect on altering blood glucose levels are contemplated for use in the invention. Accordingly, any mention of a "sulfonylurea" herein may also include such derivatives or metabolites.

Preferably the inulin preparation will have DP below about 25, more preferably in the range of from about 2 to about 23, more preferably from about 2 to about 10 or from 3 to 10, and even more preferred are inulin preparations having a significant proportion of DP in the range from about 2 to about 5 or from about 3 to about 5. Highly preferred are inulin preparations comprising a significant proportion of F2 to F5 (ie. F2=2 fructose moieties attached via β 1-2 linkage, F4=4 fructose moieties, etc.).

The sulfonylurea may be selected from Gliclazide, Glisoxepide, Glibenclamide (known also as Glyburide), Glipizide, Glimepiride, Gliquidone, Glyclopyrimide, Glibornuride, Tolazamide, Tolbutamide, Chlorpropamide, Acetohexamide, Carbutamide, Metahexamide, a derivative thereof, or combinations thereof.

Sulfonamides that are chemically similar to sulfonylurea and that have an effect on altering blood glucose levels are also contemplated and their derivatives may also be used. Such sulfonamides include, e.g., antibiotic sulfonamides such as, but are not limited to, sulfamethoxazole, sulfisomidine (also known as sulfaisodimidine), sulfacetamide, sulfadoxine, dichlorphenamide (DCP) and dorzolamide.

The improved synergistic compositions of the present invention may comprise one or more excipients, wherein at least one of said one or more excipients is inulin. In certain embodiments the compositions of the present invention comprise inulin as the sole excipient.

Preferably the compositions of the present invention are in unit dosage form, such as tablets, capsules or the like. Such unit dosage forms may contain from about 5 mg to about 50 grams of inulin. In one example the unit dose contains about 5 to 100 mg of inulin. In another example, the unit dose contains about 100 to 500 mg of inulin. In another example, the unit dose contains about 500 to about 1000 mg of inulin. In another example, the unit dose contains about 1000 to about 2000 mg of inulin. In another example, the unit dose contains about 2000 to about 3000 mg of inulin. In another example, the unit dose contains about 3000 to about 4000 mg of inulin. In another example, the unit dose contains about 4000 to about 5000 mg of inulin. In another example, the unit dose contains about 5000 mg to about 1 g of inulin. In another example, the unit dose contains about 1 g to about 2 g of inulin. In another example, the unit dose contains about 2 g to about 4 g of inulin. In another example, the unit dose contains about 4 g to about 8 g of inulin. In another example, the unit dose contains about 8 g to about 10 g of inulin. In another example, the unit dose contains about 10 g to about 15 g of inulin. In another example, the unit dose contains about 15 g to about 20 g of inulin. In another example, the unit dose contains about 20 g to about 30 g of inulin. In another example, the unit dose contains about 30 g to about 40 g of inulin. In another example, the unit dose contains about 40 g to about 50 g of inulin.

The inulin of the unit dosage form may be combined with a sulfonylurea, and/or a sulfonamide and/or derivatives and/or metabolites thereof, or combinations thereof either together in the same unit dosage form, or as separate unit dosage form, wherein the amount sulfonylurea, and/or a sulfonamide and/or derivatives and/or metabolites thereof is from about 0.5 mg to about 2000 mg, or about 1 mg to about 2 mg, or about 2.5 mg to about 5.0 mg, or about 5 mg to 10 mg, or about 10 mg to about 20 mg, or about 20 mg to about 30 mg, or about 30 mg to about 40 mg, or about 40 mg to about 50 mg, or about 50 mg to about 60 mg, or about 60 mg to about 70 mg, or about 70 mg to about 80 mg, or about 80 mg to about 90 mg or about 90 mg to about 100 mg, or about 100 mg to about 250 mg, or about 250 mg to about 500 mg, or about 500 mg to about 1000 mg, or about 1000 mg to about 1500 mg, or about 1500 mg to about 2000 mg.

Preferably the unit dosage form will contain from about 500 mg to about 2000 mg of inulin and from about 1 mg to about 30 mg of sulfonylurea and/or a sulfonamide and/or derivatives and/or metabolites thereof, or combinations thereof. Typically the unit dosage form will comprise 10 mg to 20 mg of a sulfonylurea and/or a sulfonamide and/or derivatives and/or metabolites thereof, or combinations thereof and about 500 mg inulin. Ultimately the content of sulfonylurea will depend on the type of sulfonylurea and/or a sulfonamide and/or derivatives and/or metabolites thereof, or combinations thereof used and the amount normally used for effective treatment of a patient's condition. This would be understood and well known by medical practitioners managing diabetic patients.

According to a second aspect, the present invention provides a method of prophylactic or therapeutic treatment of diabetes comprising the administration to a subject requiring such treatment of a composition comprising inulin having a DP below about 25 and a sulfonylurea or a derivative thereof, or a sulfonamide or a derivative and/or metabolites thereof.

According to a third aspect, the present invention provides a method of treating hyperglycemia comprising the administration to a subject requiring such treatment of inulin having a DP below about 25 and a sulfonylurea and/or a sulfonamide and/or derivatives and/or metabolites thereof, or combinations thereof, in the amount and for a time sufficient to reduce, regulate or normalize blood glucose concentration.

Preferably the diabetes is Type-2 Diabetes Mellitus (T2DM).

According to a fourth aspect, the present invention provides a method of preventing the development of, or ameliorating, side-effects or conditions in a subject treated with a sulfonylurea and/or a sulfonamide and/or derivatives and/or metabolites thereof, or combinations thereof, wherein the side-effects or conditions arise or are exacerbated as a result of treatment with sulfonylurea and/or a sulfonamide and/or derivatives and/or metabolites thereof, or combinations thereof, comprising the administration to a subject requiring such treatment of inulin having a DP below about 25, in the amount and for a time sufficient to prevent or ameliorate the side effects or conditions.

The side effects or conditions may be selected from hypoglycaemia, gastrointestinal disturbance, fatigue, weight gain, low mood, lack of a desire to exercise, negative changes in satiety and elevated desire to eat sweetened food or conditions associated with diabetes. Such conditions include, but are not limited to heart and blood vessel disease, nerve damage, kidney damage, eye damage, foot damage, skin and mouth conditions, low bone mineral density, Alzheimer's disease.

According to a fifth aspect, the present invention provides a method of improving efficacy of sulfonylurea treatment of diabetes in a subject receiving a sulfonylurea anti-diabetic therapy, comprising administration to said subject inulin having a DP below about 25. The improvement in efficacy of sulfonylurea action means that the normal dosage of a sulfonylurea administered to a patient may be reduced.

In this aspect, the treatment/therapy may include use of a derivative of sulfonylurea, and/or a sulfonamide and/or derivatives and/or metabolites thereof, or combinations thereof.

The subject/patient treated in accordance with the invention may be any human or mammal subject in need of such treatment. Mammal subjects/patients include, but are not limited to, apes, gorillas, chimpanzees, endangered species, stock animals, e.g., cattle, pigs, horses, and companion animals, e.g., dogs and cats.

Preferably inulin has a DP in the range of from about 2 to about 23, more preferably from about 2 to about 10 and even more preferably from about 2 to about 5. Highly preferred is inulin comprising F2 to F5 or F3 to F5.

Inulin may be administered simultaneously or sequentially, in any order, with a sulfonylurea and/or a sulfonamide and/or derivatives and/or metabolites thereof, or combinations thereof. The preferred route of administration is oral.

Conveniently, inulin may be administered as a dietary supplement in daily meals or beverages (e.g. in powder or granule form as measured sachets). Inulin may be administered as fortified or formulated food forms such as chews, bars, drinks, gums, biscuits, confectionary, breads and the like. However, it is preferred that inulin is administered in a pharmaceutical unit dosage form such as pills, tablets, caplets, tapsules or capsules, for better control of dosing and patient compliance.

The amount of inulin administered as described in any method herein may contain from about 5 mg to about 50 grams of inulin, or about 5 to 100 mg of inulin, or about 100 to 500 mg of inulin, or about 500 to about 1000 mg of inulin, or about 1000 to about 2000 mg of inulin, or about 2000 to about 3000 mg of inulin, or about 3000 to about 4000 mg of inulin, or about 4000 to about 5000 mg of inulin, or about 5000 mg to about 1 g of inulin, or about 1 g to about 2 g of inulin, about 2 g to about 4 g of inulin, or about 4 g to about 8 g of inulin, or about 8 g to about 10 g of inulin, or about 10 g to about 15 g of inulin, or about 15 g to about 20 g of inulin, or about 20 g to about 30 g of inulin, or about 30 g to about 40 g of inulin, or about 40 g to about 50 g of inulin.

The amount of inulin administered may be combined with a sulfonylurea, and/or a sulfonamide and/or derivatives and/or metabolites thereof, or combinations thereof either together or separately, wherein the amount sulfonylurea, and/or a sulfonamide and/or derivatives and/or metabolites thereof is from about 0.5 mg to about 2000 mg, or about 1 mg to about 2 mg, or about 2.5 mg to about 5.0 mg, or about 5 mg to 10 mg, or about 10 mg to about 20 mg, or about 20 mg to about 30 mg, or about 30 mg to about 40 mg, or about 40 mg to about 50 mg, or about 50 mg to about 60 mg, or about 60 mg to about 70 mg, or about 70 mg to about 80 mg, or about 80 mg to about 90 mg or about 90 mg to about 100 mg, or about 100 mg to about 250 mg, or about 250 mg to about 500 mg, or about 500 mg to about 1000 mg, or about 1000 mg to about 1500 mg, or about 1500 mg to about 2000 mg.

Preferably, the administered form will contain from about 500 mg to about 2000 mg of inulin and from about 1 mg to about 30 mg of sulfonylurea and/or a sulfonamide and/or derivatives and/or metabolites thereof, or combinations thereof. Typically the administered form will comprise 10 mg to 20 mg of a sulfonylurea and/or a sulfonamide and/or derivatives and/or metabolites thereof, or combinations thereof and about 500 mg inulin. Ultimately the content of sulfonylurea will depend on the type of sulfonylurea and/or a sulfonamide and/or derivatives and/or metabolites thereof, or combinations thereof used and the amount normally used for effective treatment of a patient's condition. This would be understood and well known by medical practitioners managing diabetic patients.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

In the context of the present invention the term "inulin" is being used interchangeably with terms "oligofructose" and/ or "fructoologosaccharide". It will be understood that more complex inulins with high DP values will contain varying proportions of inulins with low DP values, which may be referred to as "oligofructose" or "fructooligosaccharide". Such low DP value inulins may be composed of a mixture of $F_{(m)}$ and/or $GF_{(n)}$ wherein F is a fructose moiety, G is a glucose moiety and n and m is from 2 to about 10.

BRIEF DESCRIPTION OF FIGURES

FIG. 7: *Baseline FBG levels, **Inulin dose escalation, #12 gr/day inulin add-on.
FIG. 8: *Baseline FBG levels, **Inulin dose escalation, #12 gr/day inulin add-on.
FIG. 13: Schematic diagram of general manufacturing process for OFP.

DESCRIPTION OF THE PREFERRED EMBODIMENT

Figure 1:
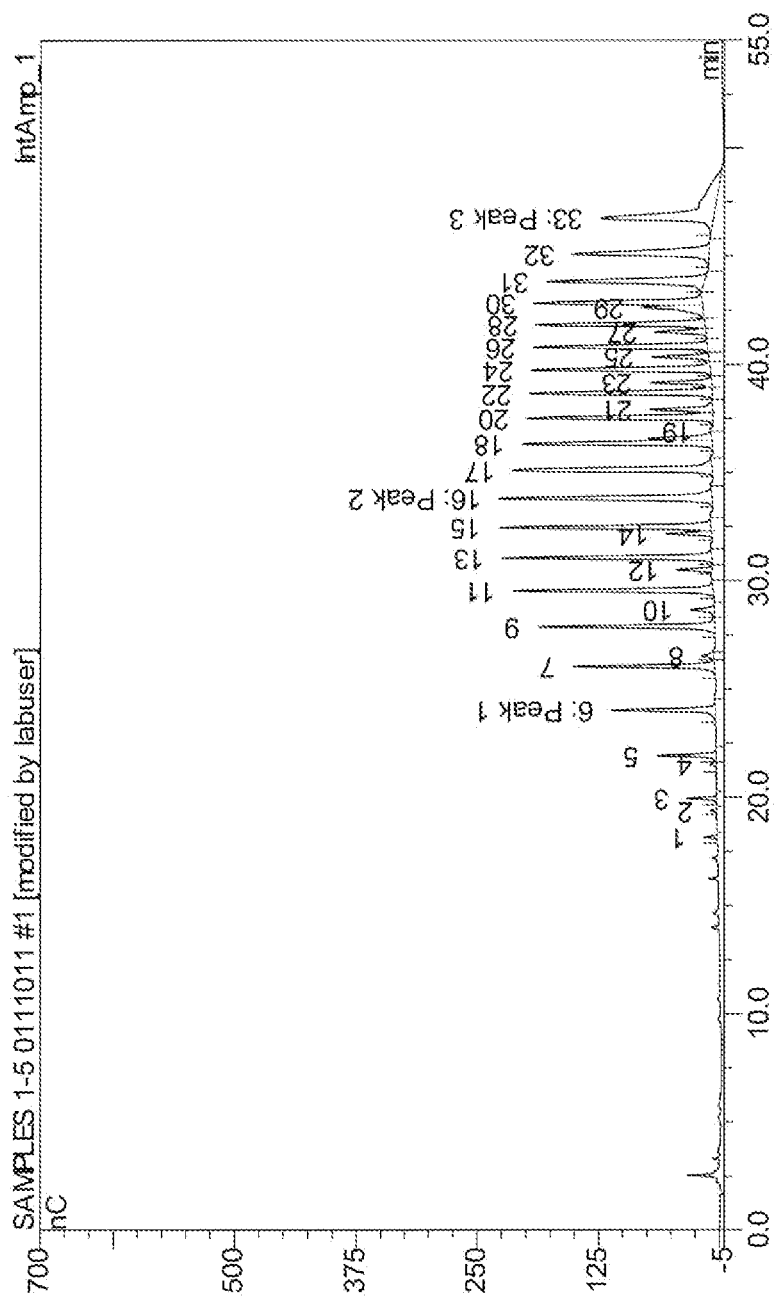
FIG. 1: Chromatogram of inulin standard

The present invention is based in part on the observation that different inulin preparations appear to synergize with sulfonylureas to different extent, judging by the dosage of inulin required to achieve effective synergy in the treatment of Type-2 Diabetes Mellitus (T2DM) patients. The present invention is concerned with assessing the useful degree of polymerization (DP) range for inulin preparations, preferably food grade, for achieving synergy with sulfonylureas in lowering or normalising FBG levels in patients with T2DM.

Oligofructose (OF) consists of a mixture of inulin fructans each comprising a terminal glucose molecule and sequentially linked fructose molecules. The fructosyl-glucose linkage is Beta-(2→1) and the fructosyl-fructose linkages are Beta-(1→2). The maximum number of fructose moieties bound (or the degree of polymerisation, ie. DP) is dependent on the source of the material. Plant, bacterial and fungal derived Oligofructose exists. Plant fructans do not exceed DP of 200, with the most common, Chicory, having an upper limit of DP value approximately 60. Bacterial fructans can have a DP as high as 100,000. Oligofructose is the partially hydrolysed, purified extract of linear fructans, obtained as native inulin, predominantly from chicory (*Cichorium intybus*) root. When derived from chicory, native inulin is purified via sequential hot water extraction, demineralisation, decolourisation, activated carbon treatment, microfiltration, & concentration, e.g., as further described in the Examples.

It has been shown herein that inulin preparations that include a proportion having a DP below about 25, and preferably in the range from about 2 to about 23 or about 3 to about 23, more preferably about 2 to about 10 or about 3 to about 10, and even more preferably about 2 to about 5, particularly F2 to F5 or F3 to F5, are likely to synergize better with sulfonylurea to lower or normalize FBG levels than inulin preparations with higher DP values. Inulin with desirable and advantageous DP values and/or with defined OF and FOS may be obtained by enzymatic treatment of inulin extracted from a suitable plant source or purchased from a commercial source, e.g., as further described in the Examples. Lower DP value inulins (eg. DP below about 25 and/or about 2 to 23 or a lower range) may be produced using different manufacturing methods well known and established in the art, and e.g., as further described herein in the Examples. Briefly, for example, by synthesizing the inulin from basic building blocks starting from sucrose (G-F) and adding fructose molecules using fructosyl transferase (Bornet 1994) (1) or by partial enzymatic hydrolysis of inulin, extracted from a natural source or obtained from a commercial source, into smaller chain lengths (De Leenheer 1996) (2). A further method for preparing low DP inulins, in particular FOS, is provided in Csanadi and Sisak 2008 (3). The resultant product is then purified, sterilized and spray dried using techniques well established in the art.

Inulin preparations of the present invention may be combined with any of the sulfonylureas currently used for the treatment of T2DM. Previous studies (PCT/AU2011/000622) have shown that inulin synergises effectively with sulfonylureas such as Gliclazide and Glibenclamide in lowering or normalizing FBG levels in T2DM patients. The present study demonstrates inulin synergy with other sulfonylureas, such as Glimepiride and Glipizide, further enforcing the original postulate that inulin synergises with any sulfonylurea. Thus, based on the chemical structure and mode of action of sulfonylureas, which may be the underlying mechanism of the observed synergy with inulin, it will be understood that inulin will synergize with other sulfonylureas such as for example Glibornuride, Glisoxepide, Gliquidone, Glyclopyrimide, Tolazamide, Tolbutamide, Carbutamide, Metahexamide, Chlorpropamide and Acetohexamide.

The amount of sulfonylurea and/or a sulfonamide and/or metabolites derivatives and/or metabolites thereof, or combinations thereof administered to a patient may be varied, including reduced, depending on a patient's response to combined treatment with an inulin preparation. This may be achieved using any standard methods known in the art for monitoring FBG levels. For example, FBG may be measured before commencing treatment and then continuously monitored at desired intervals to determine the patient's response to combined treatment with an inulin preparation. The adjustment of the amount of sulfonylurea and/or a sulfonamide and/or derivatives and/or metabolites thereof, or combinations thereof administered if required will be apparent to a medical practitioner.

Inulin may be administered to a patient receiving a sulfonylurea agent and/or a sulfonamide agent and/or derivative and/or metabolites agents thereof, or combination agents thereof either at the start of treatment with the agent, and administration continued for as long as the patient is treated with and/or a sulfonamide and/or derivatives thereof, or combinations thereof, or may be administered intermittently as required to regulate/normalize blood glucose levels. The effect of co-administration of inulin and a and/or a sulfonamide and/or derivatives thereof, or combinations thereof on blood glucose levels may not be seen in the short term and hence co-administration may need to be maintained for a period of time long enough to achieve the desired effects, for example in excess of 2 to 3 months and preferably 4 to 6 months. Based on the patient's condition, nature of treatment and response, longer periods of administration of inulin may be required before beneficial effects are noted. Of course it will be understood that such co-administration may be maintained for as long as the patient requires treatment for diabetes or hyperglycaemia.

The compositions of the present invention, in addition to being effectively used in the treatment of patients with T2DM, may also be used to treat subjects with hyperglycemia who are not yet classified as diabetic (i.e. pre-diabetic) but who are nevertheless on low level sulfonylurea treatment, so as to prevent or delay onset of diabetes.

The compositions of the present inventions can be administered by a variety of routes including oral, rectal, transdermal, subcutaneous, intravenous, intramuscular, intrathecal, intraperitoneal, intranasal and buccal. Depending on the intended route of delivery, the compounds are preferably formulated as either oral, injectable or topical compositions.

The compositions for oral administration may take the form of bulk liquid solutions or suspensions, or bulk powders and the like. For example, in case of inulin or a natural source thereof, the compositions can be in the form of a food supplement, for example a powder or a suspension that can be simply added to daily meals before consumption. It may also take the form of fresh, dried or semi-dried parts of plants, to be used in a similar manner.

The agents or compounds of the present invention may be prepared as separate compositions, for either sequential or simultaneous administration, or may be formulated together in a combination composition/unit dosage form. It will be understood that separate compositions may also each be formulated in unit dosage form. Such compositions, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

For certain applications the compositions may also be in the form of sterile injectable solutions for parenteral (including but not limited to intravenous, subcutaneous, intramuscular use). Such pharmaceutical compositions and unit dosage forms thereof may comprise ingredients in conventional proportions, with or without additional active compounds or principles, and such unit dosage forms may contain any suitable effective amount of the active ingredient(s) commensurate with the intended daily, weekly, monthly or other dosage range to be employed. Injectable compositions are typically based upon injectable sterile saline or phosphate-buffered saline or other injectable carriers known in the art.

The amount of each composition actually administered will typically be determined by a physician in the light of the relevant circumstances, including the condition to be treated, the chosen route of administration, the actual compound(s) administered, the age, weight, and response of the individual patient, the severity of the patient's symptoms/condition, and the like.

The above described components for orally administered or injectable compositions are merely representative. The composition may be formulated for administration. Processing techniques known in the art maybe used, as well as known pharmaceutically acceptable carriers, diluents or excipients. To prepare such formulations, compositions described herein, containing active ingredient(s) are mixed with a pharmaceutically acceptable carrier or excipient for example, by mixing with physiologically acceptable carriers, excipients, or stabilizers in the form of, e.g., lyophilized powders, slurries, aqueous solutions, or suspensions (see generally Remington's Pharmaceutical Sciences, (4) and e.g., references (5) to (10) and the Examples.

The compounds of the present invention can also be administered in sustained release forms or from sustained release drug delivery systems, either in separate dosage forms or in a combination dosage form. A description of representative sustained release materials can also be found in the incorporated materials in Remington's Pharmaceutical Sciences, and e.g., references (5) to (10). Such administration can also occur via bolus administration, or via implantable devices, or patches or the like.

Preferably, the compositions are presented in unit dosage forms to facilitate accurate dosing. The term "unit dosage forms" refers to physically discrete units suitable as unitary dosages for human subjects and other mammals (for example companion animals or stock animals, or any other animal as described herein), each unit containing a predetermined quantity of active material calculated to produce the desired therapeutic effect, in association with a suitable pharmaceutical excipient e.g., as described in the Examples. Typical unit dosage forms include prefilled, premeasured ampoules or syringes of the liquid compositions or pills, tablets, capsules, caplets, tapsules or the like, in the case of solid compositions.

The unit dosage forms of the present invention, such as a tablet or capsule, may comprise from 0.5 to about 2 g of a sulfonylurea and about 5 mg to about 50 g of inulin, or as described herein. In practice however, a typical dosage form may comprise about 1 mg to 2 mg of a sulfonylurea and/or a sulfonamide and/or derivatives and/or metabolites thereof, or combinations thereof, and about 500 mg of inulin. In a typical treatment regimen this would mean taking about 4 unit dosage forms three times a day to achieve the desired therapeutic effect (eg. lowering blood glucose levels). However, depending on the exact nature of inulin and its compressibility (in case of a tablet unit dosage form), higher amounts of inulin may be used, for example 2000 mg, or even more, per dosage form, thus reducing the number of dosage forms that need to be taken in order to achieve the desired therapeutic effect.

In the compositions of the present invention, particularly when they are in unit dosage form, inulin may also serve as one of a number of excipients or may be the sole excipient in the formulation, thus acting as both an active and an excipient.

Further design and inclusion criteria are also contemplated based on the ability of one or more additional substances that may be added to compositions to facilitate or synergise the dosage of the composition via, for example, release modifying agents that may include physical and/or chemical modifications to the formulation. Physical modifications may include, e.g., dispersion agents, gas generation substances, size and structure modifications or selections including nanoparticles. Chemical modifications may include e.g., pH modification agents, buffers, co-solvents, polymers, plasticizers. Metabolism modifying agents may also be included, e.g., fats, proteins, carbohydrates, salts, minerals, as well as substances known to affect the GI (Glycemic index), competitors for drug binding sites, enzyme inhibitors, enzymes, hormones and the like.

Co-medications or substances that redress or modify the adverse effects of sulfonylureas such as vascular attack, pancreatic depletion; or vitamin, mineral or other nutritive substances may also be added to the compositions of the invention, or further administered in the methods or use of the invention.

The present invention will now be described in more detail with reference to specific but non-limiting examples describing specific compositions and methods of use. It is to be understood, however, that the detailed description of specific procedures, compositions and methods is included solely for the purpose of exemplifying the present invention. It should not be understood in any way as a restriction on the broad description of the inventive concept as set out above.

EXAMPLES

Example 1

Analytical Testing of Inulin Preparations

The analyses of inulin preparations were performed by Australian Proteome Analysis Facility (Research Park Drive, Macquarie University, Sydney, NSW, 2109, Australia), as briefly described below.

Standard and Sample Details:

For convenience, all inulin samples/preparations were purchased from commercial sources. Inulin standard was purchased from Sigma Aldrich (PN: 12255-10G, LN: 099F71251V) and four different inulin preparations, namely Orafti HP, Orafti GR, Orafti P95, all obtained from Orafti Inc., Belgium, and a commercially available inulin (CI), (obtained from Just Like Sugar, Inc., Las Vegas, Nev., USA), were analysed.

Analysis Procedure:

A standard inulin solution and four inulin preparation were prepared at a concentration of 1 mg/ml by dissolving in hot MilliQ water and cooling to room temperature before use. A solution of each was made fresh each day and analysed under identical conditions. All samples and standards were performed on 3 consecutive days. The analysis of the standard and each sample was conducted over 3 separate runs according to the schedule below:

Standard and inulin samples were freshly prepared for each at different days at 1 mg/ml. Inulin solvent (MilliQ water) was used as a blank. The instrument was set to run the samples in the following sequence:

Standard, blank, any SAMPLE, blank, any SAMPLE, blank, any SAMPLE, blank, any SAMPLE, blank, any SAMPLE, blank, Standard.

Instrument and Method:

The analyses of the standard and 4 samples were undertaken on a Dionex high-performance anion-exchange chromatography system with pulsed amperometric detection (HPAEC-PAD)—(Dionex Pty Ltd, Lane Cove, Australia).

Method:

Guard Column: CarboPac PA200 guard column (3×50 mm)

Column: CarboPac PA200 column (3×250 mm)

Column Temperature: 30° C.

Injection volume: 25 µL

Flow rate: 0.5 mL/min

Solvents: A=100 mM NaOH

B=500 mM $CH_3COONa$ in 100 mM NaOH

C=MilliQ water

D=200 mM NaOH

Gradient:

| Time (min) | % A | % B | % C | % D |
|---|---|---|---|---|
| 0 | 77.6 | 2.4 | 0 | 20 |
| 5 | 77.6 | 2.4 | 0 | 20 |
| 40 | 56 | 24.0 | 0 | 20 |
| 45 | 56 | 24.0 | 0 | 20 |
| 55 | 77.6 | 2.4 | 0 | 20 |

Quality, Accuracy and Precision of the Results:

All three runs demonstrated identical results for the inulin standard and the four inulin preparations tested. Three peaks were selected as reference points (to assess performance of the system such as accuracy, precision etc.), one at the front, one in the middle and one at the end of the profile. Analysis of these peaks, from each sample across the three runs showed a % RSD<1% for the retention time and <5% for the number of peaks detected. The area and height varies between each replicate analysis due to deviation in sample weights. The number of peaks detected, peak area and height is dependent on parameters set in the Dionex Chromeleon software.

The numbers above the chromatogram peaks are for labeling and referral purposes only. By way of brief explanation, when a peak is integrated the system software places a number above the peak. Thus, the peak labeled "1" in each of the chromatograms corresponds to peak "1" in a table from which the chromatograms are and allows a cross-reference to the data associated with that peak. The X axis units are retention time and the Y-axis units are nC (nano-Coulombs).

Inulin standard from Sigma Aldrich was used to standardize the instrument (FIG. 1). Once standardized the instrument with the exact same procedure/method was used to evaluate the chromatogram for each inulin preparation that was used in the treatment of the T2DM patient.

Example 2

Glibenclamide/Inulin Co-Therapy in T2DM Patient—Effect of Different Inulin Preparations Clinical Data:

The patient data provided herein has been obtained in accordance with the methodology and procedures described in PCT/AU2011/000622, incorporated herein by reference.

Subject:

65 years old female, with body mass index of 30 classified as obese, with the history of T2DM, atrial fibrillation, high blood pressure, high blood cholesterol and osteoarthritis.

Medical History:

At the age of 49 the patient was diagnosed with T2DM. The patient was treated for diabetes with Glibenclamide (Alphapharm Pty Ltd) (3×5 mg/day=15 mg/day).

OTC or Other Supplements:

| Inulin: | 12 grams/day | 4 grams-3 times a day |
|---|---|---|

The sources of inulin preparations are described above in Example 1.

Glucose Measurements:

Blood glucose level was determined using Accu-Chek Performa (Roche, Mannheim, Germany) device (CAT/TYP 04680464002 mmol/L and 55404204955) according to manufacturer instructions. Other similar devices can also be used.

Figure 2:
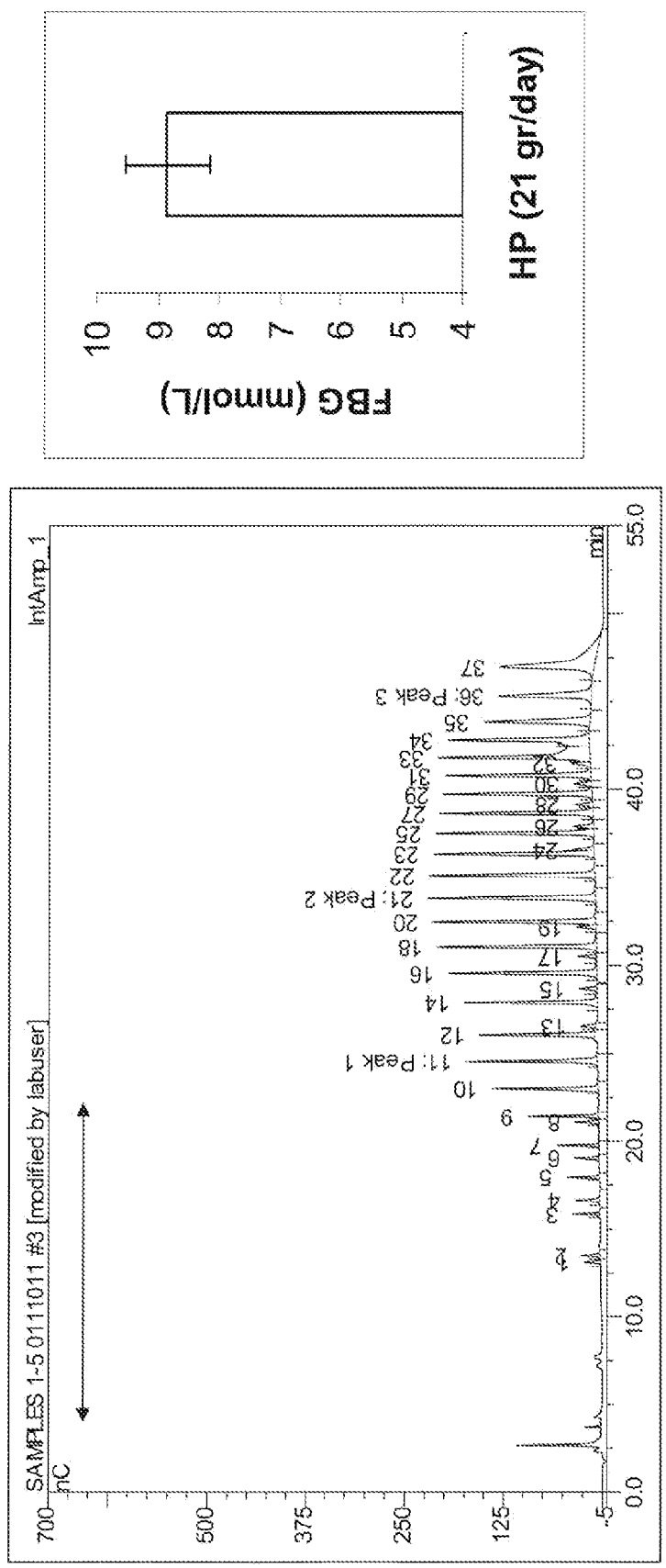
FIG. 2: Chromatogram of Orafti HP inulin (arrow indicates a DP range of about 2 to 10) and corresponding effect of this preparation on the FBG level of a patient with T2DM.

Results:

Effect of Orafti HP preparation:

Prior to intake of Orafti HP inulin, patient consumed CI at 15 g/day with average monthly FBG levels of 5.7±0.21 mmol/L (not shown). After one month of consumption of ~21 g/day, the food grade Orafti HP inulin preparation that is characterized by a DP range of above 23 resulted in a dramatic increase in FBG levels from 5.7±0.21 mmol/L to monthly average of 8.8±0.7 mmol/L. The chromatogram of the inulin preparation and corresponding effects of this inulin preparation on patient's FBG level is shown in FIG. 2. Due to this increase, consumption of Orafti HP inulin was terminated and patient continued to take CI (characterized by a DP range of about 2 to 60) until the FBG levels returned to normal. Patient claimed that during Orafti HP inulin intake the symptoms of diabetes, such as lethargy, sweating, muscle weakness and pain had returned.

Figure 3:
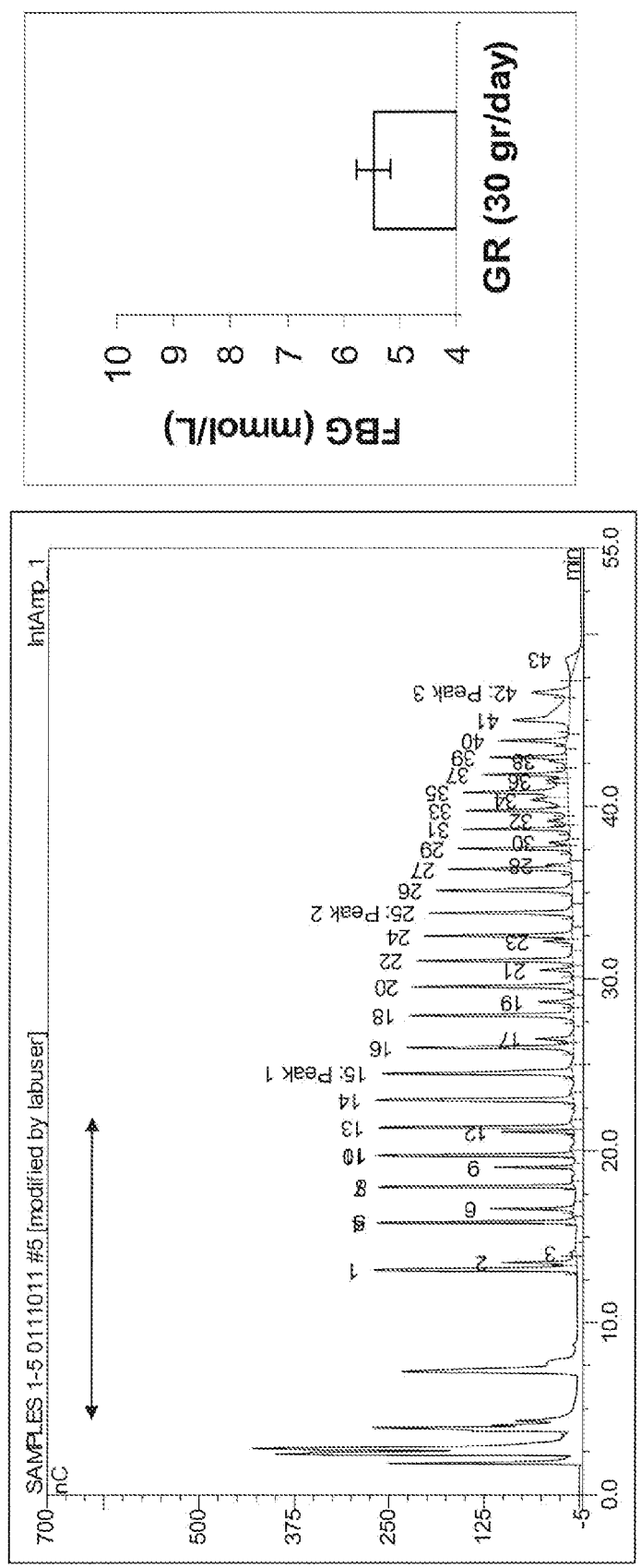
FIG. 3: Chromatogram of Orafti GR inulin (arrow indicates a DP range of about 2 to 10) and corresponding effect of this preparation on the FBG level of a patient with T2DM.

Effect of Orafti GR Preparation:

Prior to intake of Orafti GR inulin, patient consumed CI at 15 g/day with average monthly FBG levels of 5.2±0.2 mmol/L. After one month of consumption of ~15-21 g/day, the food grade Orafti GR inulin preparation that is characterized by a DP range of between about 10-60 (certain amount of inulin with values for DP lower than 10 was also present) resulted in increased FBG levels from 5.2±0.2 mmol/L to 6.8±0.2 mmol/L. Further increasing Orafti GR intake to 30 g/day resulted in normalization of FBG levels. The chromatogram of the inulin preparation and corresponding effects of this inulin preparation on patient's FBG level is shown in FIG. 3. Patient claimed feeling well during consumption of this high dose of Orafti GR.

Figure 4:
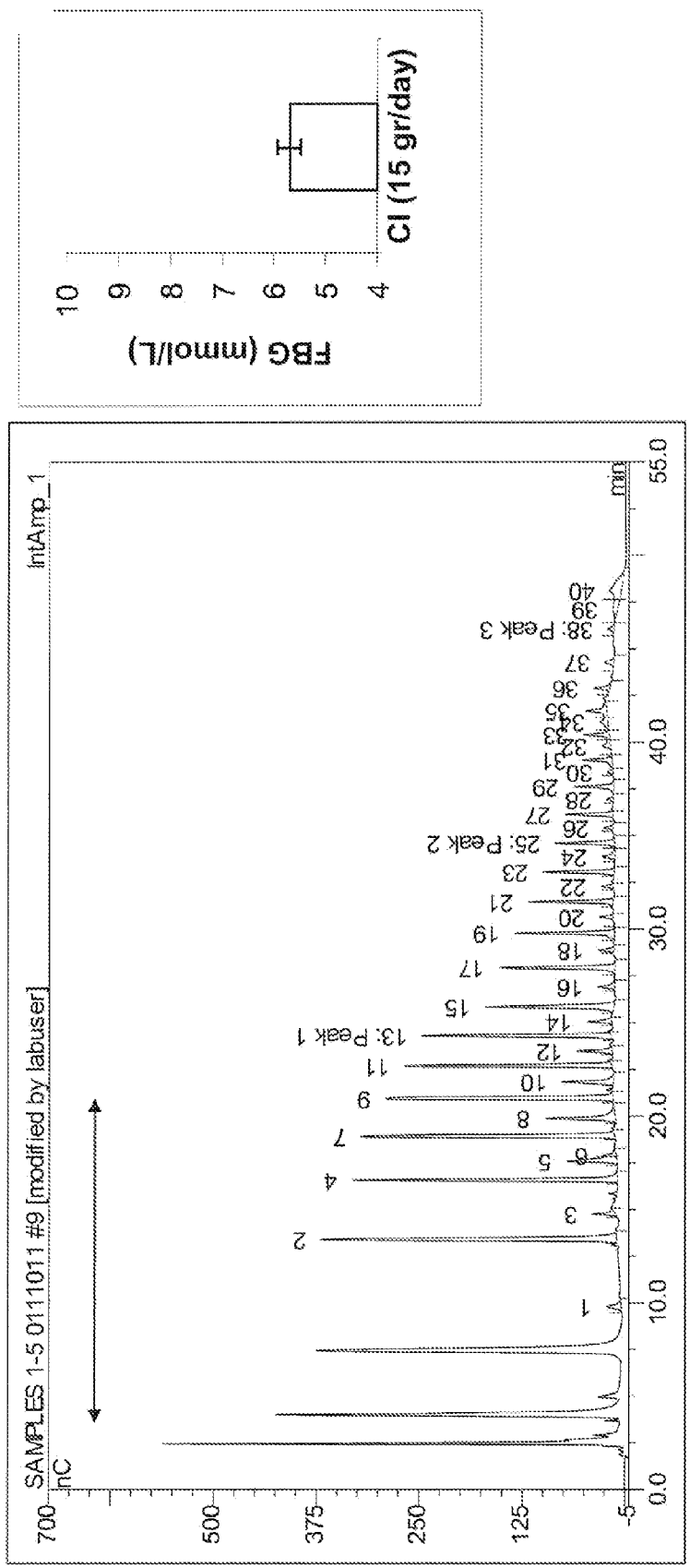
FIG. 4: Chromatogram of a commercially available inulin (Cl) (arrow indicates a DP range of about 2 to 10) and corresponding effect of this preparation on the FBG level of a patient with T2DM.

Effect of CI Inulin Preparation:

Patient, as described above, consumed CI at 15 g/day with normalization of FBG levels at all times. The chromatogram of this inulin preparation and corresponding effects of this inulin preparation on patient's FBG level is shown in FIG. 4.

Figure 5:
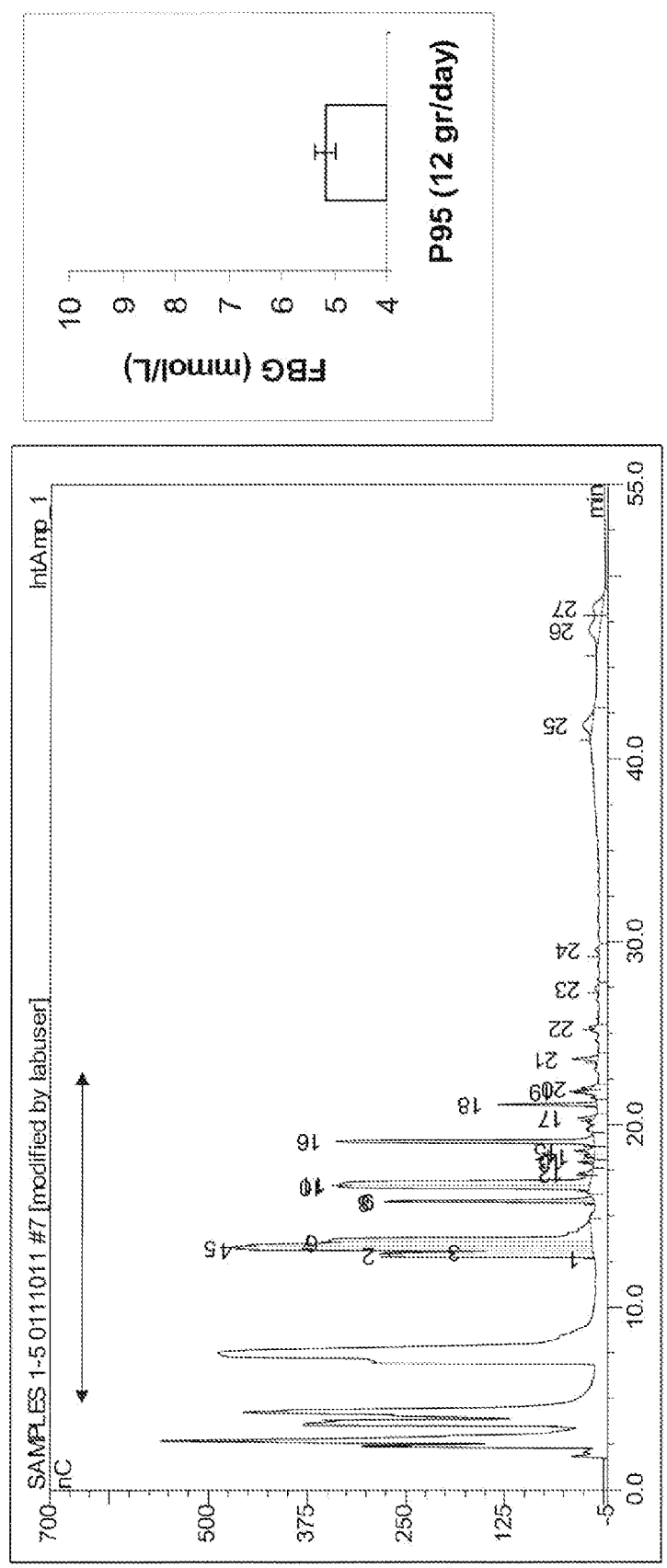
FIG. 5: Chromatogram of Orafti P95 inulin (arrow indicates a DP range of about 2 to 10) and corresponding effect of this preparation on the FBG level of a patient with T2DM.
Figure 6:
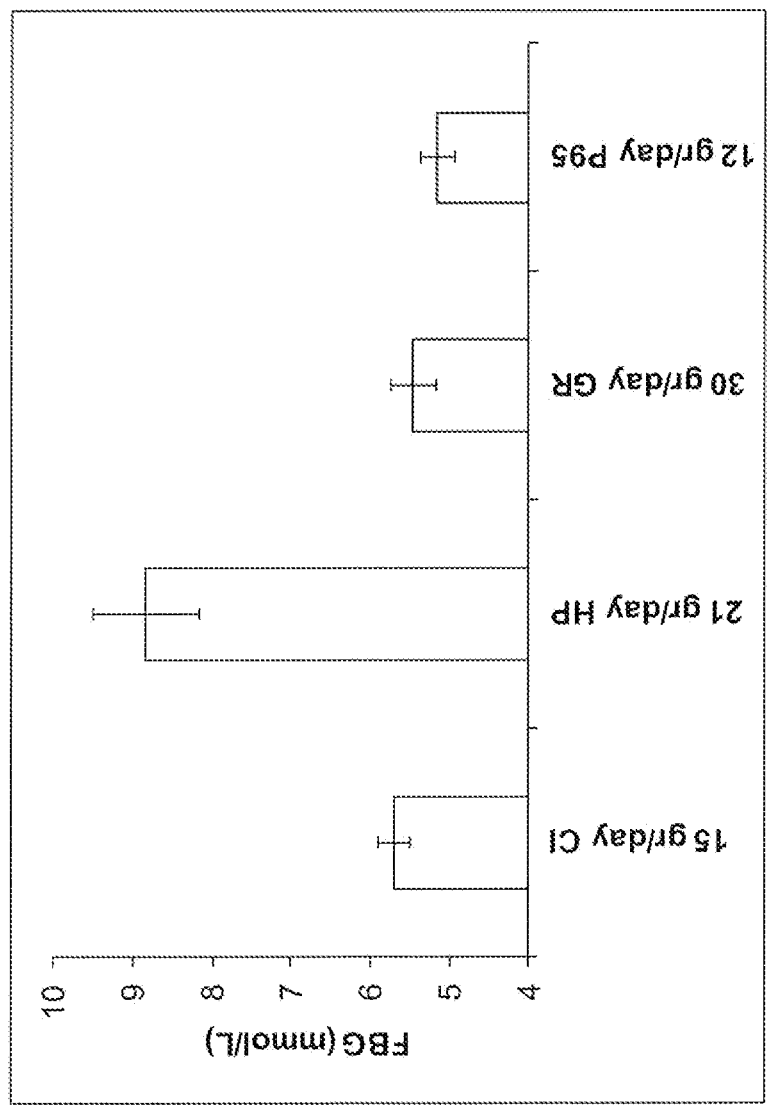
FIG. 6: Comparison of effects of different inulin preparations on FBG level of a patient with T2DM.

Effect of Orafti P95 Preparation:

Prior to intake of Orafti P95 inulin, patient consumed CI at 15 g/day with average monthly FBG levels of 5.4±0.3 mmol/L. After one month of consumption of ~12 g/day, the food grade Orafti P95 inulin preparation that is characterized by a DP range of between 3-10 provided normal FBG levels. The chromatogram of Orafti P95 inulin preparation and corresponding effects of this inulin preparation on patient's FBG level is shown in FIG. 5. Patient has claimed that during Orafti P95 she felt very well and no symptoms of diabetes occurring. She claims that this preparation provided best effect with respect to diabetic symptoms.

Discussion:

Comparison of the effects of different inulin preparation on a type 2 diabetes mellitus patient demonstrated that inulin preparations with a lower DP range provide better synergy with sulfonylurea in normalizing FBG levels.

Normalization of FBG levels by Orafti GR required higher amounts of this inulin to be consumed (at ~30 g/day). Since approximately half of this preparation (compare the chromatogram in FIG. 3 with FIG. 2 and FIG. 4, range represented by an arrow) possessed inulin with DP below 23, twice the amount of this preparation was required for normalization of FBG when compared to CI (15 g/day). On the other hand CI contained more inulin with DP below about 23 (approximately 70-80%) which resulted in better synergisms with sulfonylurea.

In contrast to the above results, normalization of FBG by Orafti P95 required lower amounts of this inulin to be consumed (at ~12 g/day). Since all of this preparation (compare the chromatogram in FIGS. 2-5) possessed inulin with DP below about 10, even slightly lower amounts of this preparation were required for normalization of FBG when compared to CI (15 g/day).

Overall Findings:

From these findings it is clear that inulin with lower DP range, for example below about 23 but preferably in the range of about 2 to 23 and more preferably in the range of about 2-10, and even more preferably from about 2 to about 5. Highly preferred is inulin comprising F2 to F5 provides better synergy with sulfonylurea than higher DP ranges, eg. above about 23 (see FIGS. 2 to 6)

Example 3

Glimepiride/Inulin Combination Therapy for Type 2 Diabetes Mellitus: A Case Report Subject:

59 years old female, with body mass index of 33 classified as obese, with the history of T2DM, and osteoarthritis.

Medical History:

At the age of 55 the patient was diagnosed with T2DM. Doctor recommended diet-only treatment. At age 57 due to increased FBG levels the patient was treated with Glimepiride (1 mg/day, 1 mg once daily). The dose was increased in a 1 mg increment and currently this patient is taking 4 mg once daily Glimepiride.

OTC or Other Supplements:

| Glucosamine | 1500 mg/day | twice daily |
| Inulin (CI): | 12 grams/day | 4 grams-3 times a day |

Figure 7:
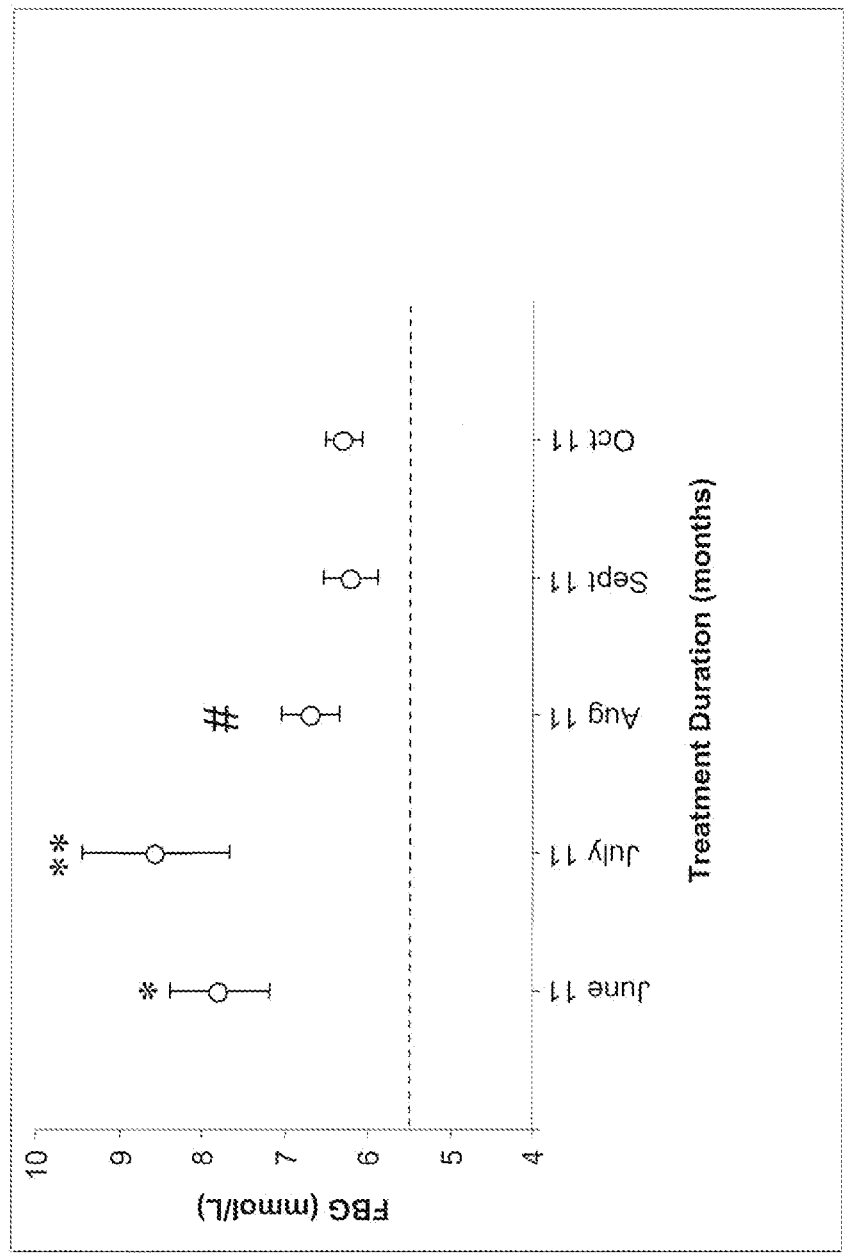

Methods:
Glucose Measuring Device:
Blood sugar level was determined using Accu-Chek Performa (Roche, Mannheim, Germany) device (CAT/TYP 04680464003 mmol/L and 55405079196) according to manufacturer instructions.
Results:
The efficacy of inulin on Glimepiride monotherapy was investigated. A couple of years prior to inulin combination therapy, patient's FBG level fluctuated and was uncontrolled above 7 mmol/L. FIG. 7 depicts the monthly FBG level average at indicated time points. Conditions of treatments are described below:
June 2011:
During baseline measurements of FBG levels, patient was on Glimepiride at the dose of 4 mg once daily.
July 2011:
Inulin introduced at 3 gr/day (1 gr with each meal, 3 times a day) for one week. Inulin amount was increased to 6 gr/day (2 gr with each meal, 3 times a day) at week 2, 9 gr/day (3 gr with each meal, 3 times a day) at week 3 and 12 gr/day (4 gr with each meal, 3 times a day) at week 4.
August-October 2011:
Patient continued taking Inulin with each meal at 4 gr/meal (12 gr/day total). The data demonstrates ~2 mmol/L reduction, from ~8 mmol/L at baseline to ~6 mmol/L at the end of 3 months Inulin intake. Results are shown in FIG. 7.
The FBG level of the patient is restored to near normal levels when inulin was consumed at approximately 12 grams/day in combination with Glimepiride. The patient also claims that consumption of inulin boosted energy, increased bowel movements, alleviated muscle pains, and overall provided a better quality daily life.

Example 4

Glipizide/Inulin Combination Therapy for Type 2 Diabetes Mellitus: A Case Report Subject:
54 years old male, with body mass index of 29 classified as overweight, with the family history of T2DM.
Medical History:
At the age of 50 the patient was diagnosed with T2DM. Doctor recommended diet-only treatment. At age 52 due to increased FBG levels the patient was treated with Glipizide (5 mg/day, 5 mg once daily). The dose was increased in a 5 mg increment and currently this patient is taking 15 mg/day, 5 mg three times a day, Glipizide.
Other Supplements:

| Inulin (CI) | 12 grams/day | 4 grams-3 times a day |

Methods:
Glucose Measuring Device:
Blood sugar level was determined using Accu-Chek Performs (Roche, Mannheim, Germany) device (CAT/TYP 04680464002 mmol/L and 55403057614) according to manufacturer instructions.

Figure 8:
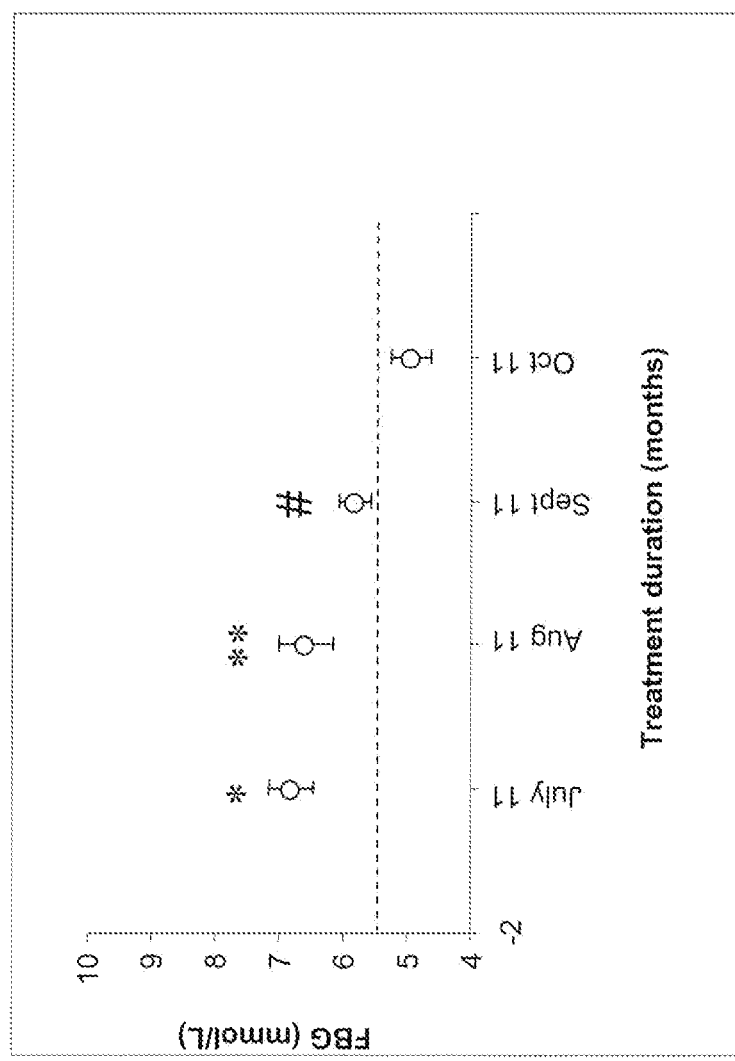

Results:
The efficacy of inulin on Glipizide monotherapy was investigated. A couple of years prior to inulin combination therapy, patient's FBG level was reasonably controlled around 7 mmol/L. FIG. 8 depicts the monthly FBG level average at the indicated time points. Conditions of treatments are described below:
July 2011:
During baseline measurements of FBG level, patient was on Glipizide at the dose of 15 mg per day.
August 2011:
inulin introduced at 3 g/day (1 g with each meal, 3 times a day) for one week. Inulin amount was increased to 6 g/day (2 g with each meal, 3 times a day) at week 2, 9 g/day (3 g with each meal, 3 times a day) at week 3 and 12 g/day (4 g with each meal, 3 times a day) at week 4.
September-October 2011:
Patient continued taking inulin with meal at 4 g/meal (12 gr/day total). The data demonstrates ~1.5 mmol/L reduction, from ~6.5 mmol/L at baseline to ~5 mmol/L at the end of 2 months inulin intake. Results are shown in FIG. 8.
The FBG level of the patient is restored to normal levels when inulin is consumed at approximately 12 g/day in combination with Glipizide. The patient also claims that consumption of inulin, increased bowel movements, and overall provided a better quality of life with increased energy levels resulting in increased daily walks and exercise.

Example 5

Figure 9:
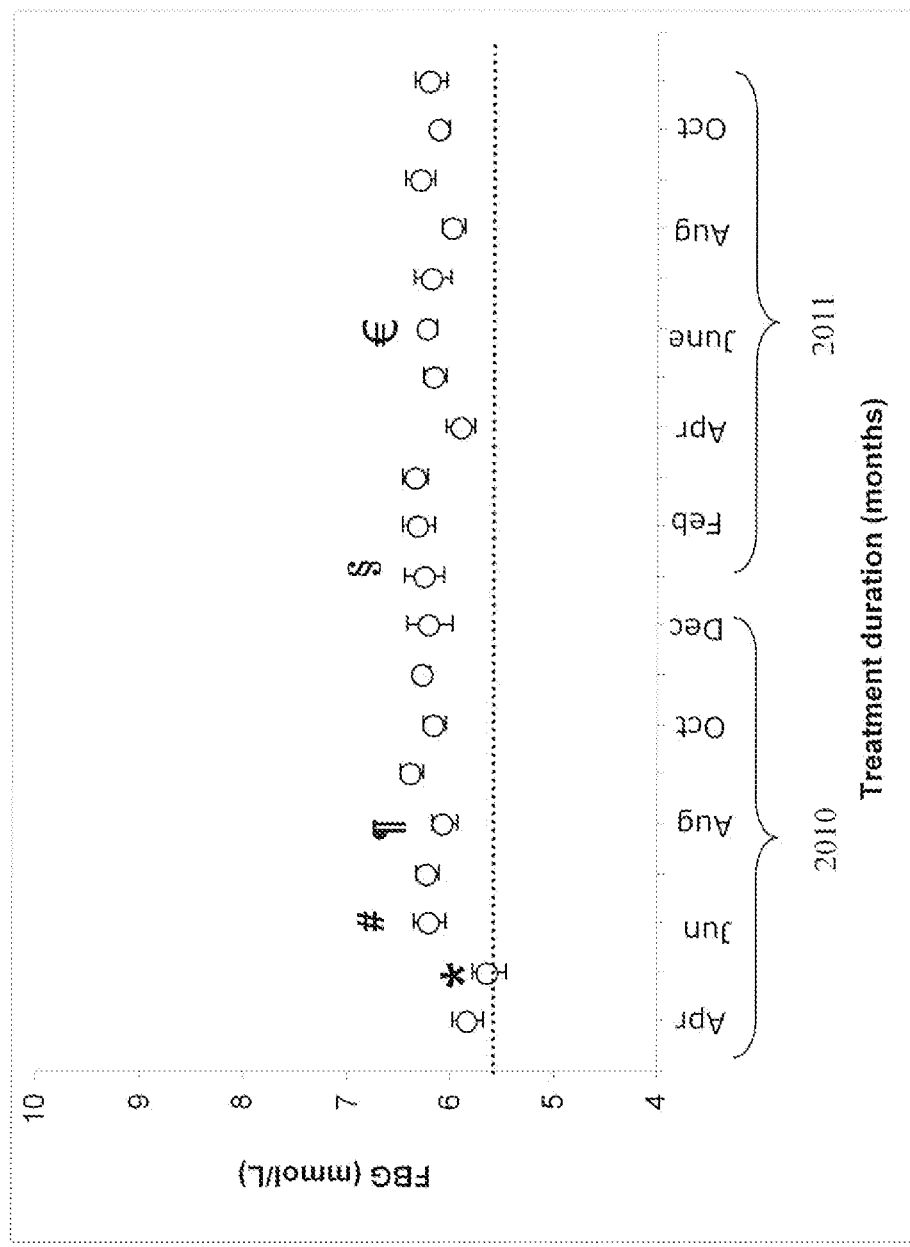
FIG. 9: FBG level profile of a pre-diabetic subject during and after cessation of treatment with inulin. (¶) commercially available inulin (Cl); (§) inulin (Orafti GR), (€) discontinued treatment with inulin.

Effect of Inulin Monotherapy and its Withdrawal on Fasting Blood Glucose Levels of a Pre-Diabetic Individual: A Case Report Subject:
46 years old male, with body mass index of 28 classified as overweight, with the family history of T2DM.
Methods:
Glucose Measuring Device:
Blood sugar level was determined using Accu-Chek Performa (Roche, Mannheim, Germany) device (CAT/TYP 04680464003 mmol/L and 55405441515) according to manufacturer instructions.
This subject, who was predisposed to diabetes but not treated with any anti-diabetic medication, and who had FBG levels above normal limits (approx. 6.0 mmol/L), also consumed inulin, first inulin (CI) (¶) then inulin (Orafti GR) (§), for 13 months. In contrast to patients who were under sulfonylurea treatment, the consumption of 12-15 g/day of inulin over the period of 13 months did not change the levels of FBG in this subject. Discontinuation of inulin (€) for six month did not result in any significant changes in FBG levels of this individual (FIG. 9).

Example 6

Figure 10:
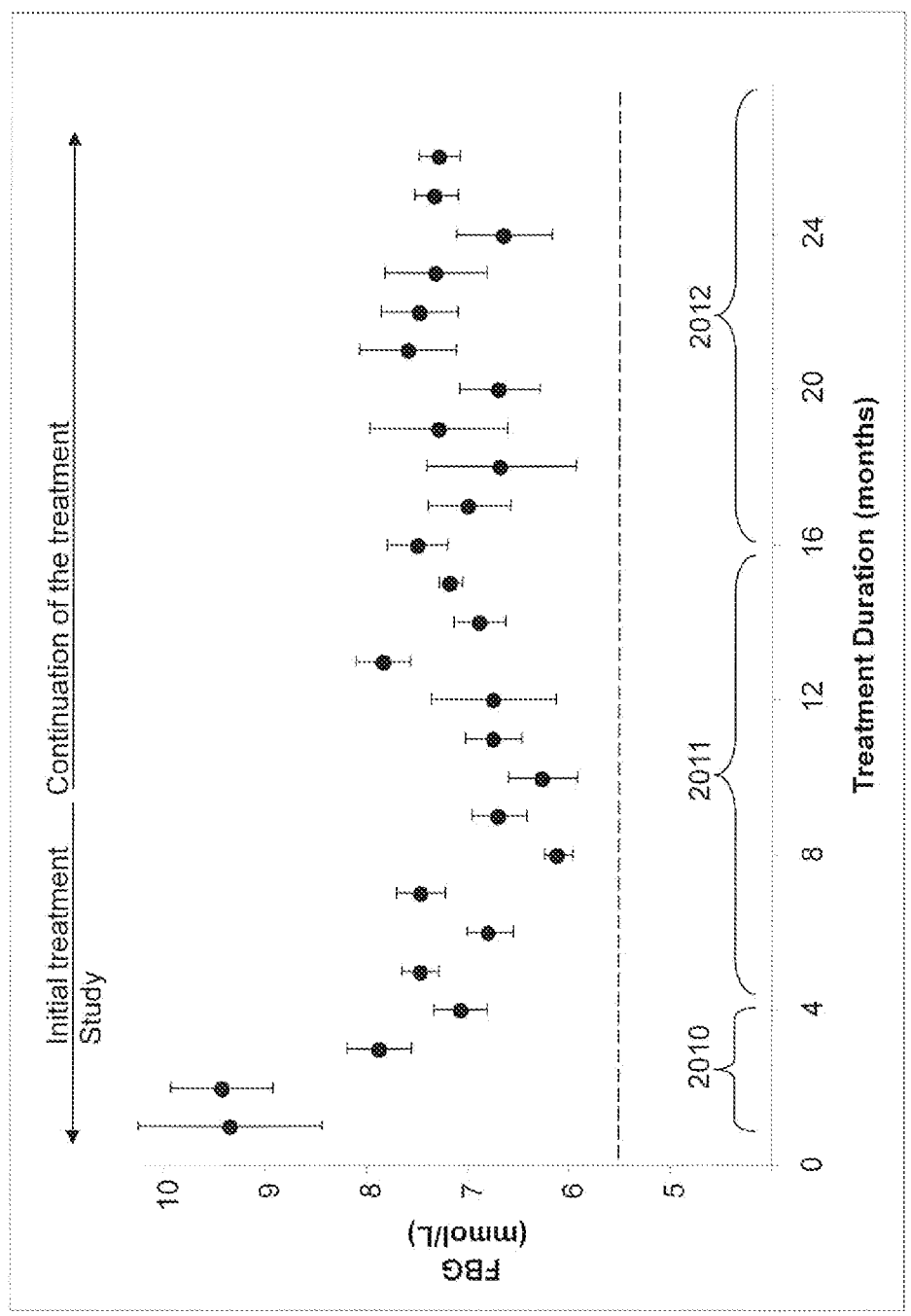
FIG. 10: Continued effect of inulin on FBG levels in a patient on Gliclazide monotherapy in combination with 15 gr/day of inulin (Cl); The graph shows the initial treatment study as previously shown in FIG. 2 of PCT publication WO 2011/146981 (left portion as labelled), which was further continued beyond 24 months (right portion as labelled).

Gliclazide/Inulin Combination Therapy for Type 2 Diabetes Mellitus: A Case Report This Example shows extended data from a patient, who was under Gliclazide therapy (30 mg, once daily) for nearly a decade with uncontrolled blood glucose levels above 9 mmol/L. This patient began the combination therapy with a commercially available inulin (CI) as previously described in PCT/AU2011/000622, the contents of which are incorporated herein in their entirety. Various blood parameter measurements were as described PCT/AU2011/000622. The results are shown in FIG. 10 and Table 1 below demonstrating the efficacy of inulin combination therapy is sustained beyond 24 months.

TABLE 1

FBG, HA1C and Lipid profiles of the patient performed by an independent pathology laboratory.

|  | 22/07/2008 | 20/04/2009 | 17/12/2010 | 16/05/2011 | 19/10/2011 | 10/07/2012 | 23/10/2012 |
|---|---|---|---|---|---|---|---|
| Fasting Glucose (Normal 3-5.5 mmol/L) | 6.0 | 7.7 | 7.4 | 5.1 | 7.3 | 7.5 | 8.2 |
| HA1c (Normal <7%) | 7.0 | 7.2 | 7.8 | 7.2 | 7.6 |  | 7.2 |
| Cholesterol (Normal 3.1-5.1 mmo/L) | 4.4 | 4.2 | 2.9 | 4.4 | 4.7 | 4.8 | 4.3 |
| Triglycerid (Normal 0.5-2 mmol/L) | 1.2 | 1.5 | 0.8 | 1.2 | 0.9 | 1.4 | 0.9 |
| HDL (Normal >1 mmol/L) | 1.0 | 1.2 | 1.1 | 1.2 | 1.4 | 1.3 | 1.4 |
| LDL (Normal 0-3.5 mmol/L) | 2.9 | 2.3 | 1.4 | 2.6 | 2.9 | 2.9 | 2.5 |
| Coronary risk ratio (Normal <5) |  |  | 2.6 |  | 3.4 | 3.7 | 3.1 |

Example 7

Figure 11:
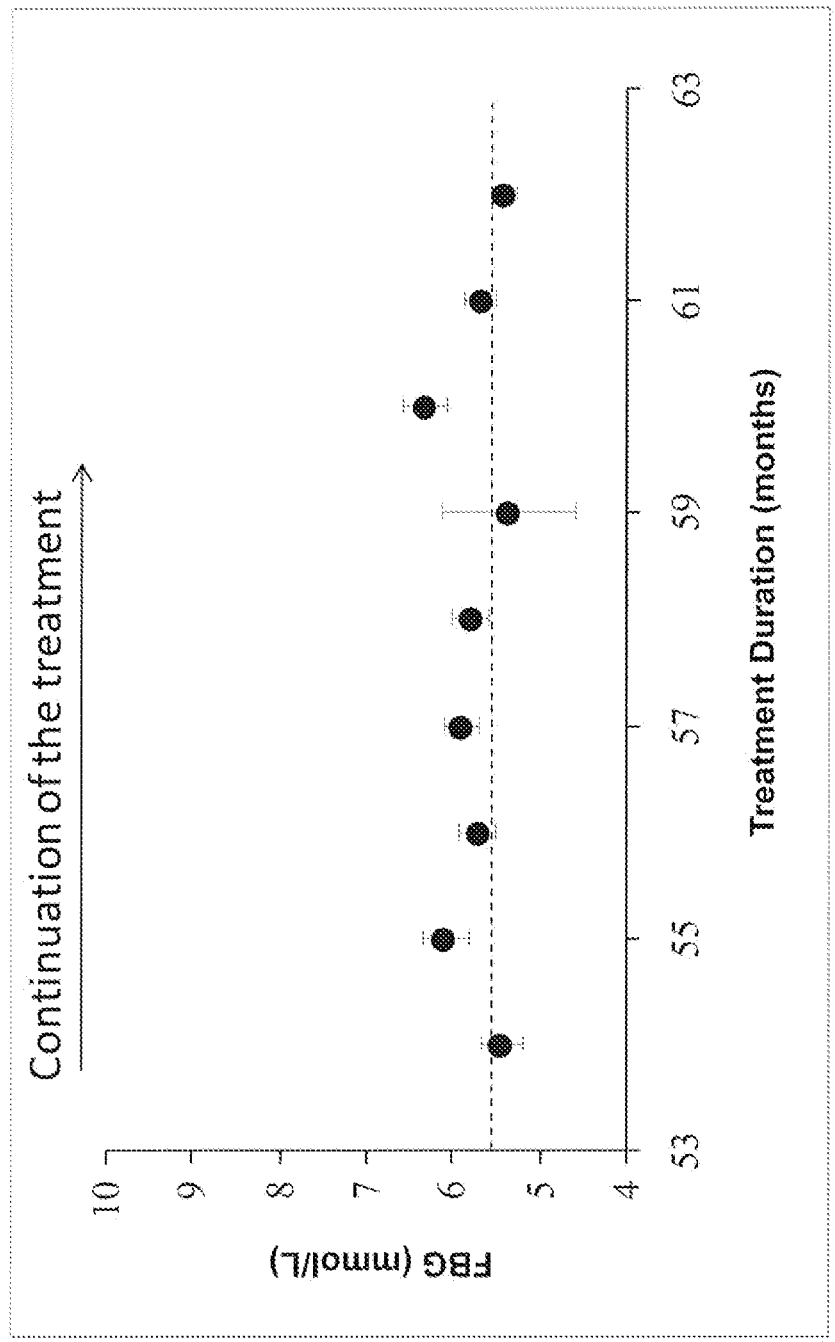
FIG. 11: Continued effect of inulin on FBG levels in a patient on treatment with sulfonylurea, Glibenclamide, mono therapy in combination with 15 gr/day of Cl; The graph shows continued treatment beyond 61 months (as labelled) and is a continuation of the treatment study shown in FIG. 3 of PCT publication WO 2011/146981.

Glibenclamide/Inulin Combination Therapy for Type 2 Diabetes Mellitus: Evaluation of extended efficacy for over 62 weeks This Example shows extended data from a patient as described in Example 3 of PCT/AU2011/000622 who continued taking CI for an extended period of time (over 5 year), and combination therapy with Glibenclaminde (5 mg, three times daily) and continued following a similar protocol as described Maintaining the patient on combination therapy with this inulin preparation has normalized the FBG levels and maintained them within the normal range. The results of this study are shown in FIG. 11 and Table 2 below. Various blood parameter measurements were as described PCT/AU2011/000622. The results are shown in FIG. 11 and Table 2 below demonstrating the efficacy of inulin combination therapy is sustained beyond 63 months. Maintaining the patient on combination therapy with this inulin preparation has normalized the FBG levels and maintained them within the normal range.

TABLE 2

FGL, HA1C and Lipid profiles of a patient who was on CI add-on and glibenclamide monotherapy

|  | 5/11/2006 | 31/05/2008 | 1/10/2008 | 12/12/2008 | 24/10/2009 | 2/03/2010 | 7/03/2010 | 27/04/2010 | 17/01/2011 | 7/03/2011 | 2/09/2011 |
|---|---|---|---|---|---|---|---|---|---|---|---|
| Fasting Glucose (Normal 3-5.5 mmol/L) | 10 | 6 | 6.3 | 5.1 | 7 | 6.4 |  |  | 5.4 | 7.5 | 6.9 |
| HA1c (Normal <7%) |  | 6.5 | 7 |  | 6.6 |  | 6.9 | 6.9 | 6.8 | 6.9 | 6.5 |
| Cholesterol (Normal 3.1-5.1 mmo/L) | 6.2 | 3.1 | 3.6 | 3.8 | 4.4 | 4.4 |  |  | 3.8 |  | 4.3 |
| Triglycerid (Normal 0.5-2 mmol/L) | 4 | 1.1 | 1 | 1 | 1 | 1.6 |  |  | 1.5 |  | 1.2 |
| HDL (Normal >1 mmol/L) |  | 1.2 | 1.2 |  | 1.4 | 1.3 |  |  | 1.1 |  | 1.6 |
| LDL (Normal 0-3.5 mmol/L) |  | 1.4 | 1.9 |  | 2.5 | 2.4 |  |  | 2 |  | 2.1 |
| Coronary risk ratio (Normal <5) |  | 2.6 | 3 |  | 3.1 | 3.4 |  |  |  |  |  |

Example 8

Example of Compositional Guideline for Oligofructose Preparations and Naming of Different Molecular Structures

TABLE 3

Oligofructose content of different inulin preparations (including guide to oligofructose terminology). The relative concentrations of the oligofructose has been determined at the Australian Proteome Analysis Facility.

| Short Name | General name | Names (a) | (b) | CAS | Relative conc. (%) | |
|---|---|---|---|---|---|---|
| G | Glucose |  |  | 921-60-8 | 0.5 ± 0.4 | 4-12% |
| F | Fructose |  |  | 30237-26-4 | 3.1 ± 0.3 | |
| GF | Sucrose |  |  | 57-50-1 | 3.9 ± 1.4 | |
| $GF_2$ | Difructooligosaccharide | Kestose | trisaccharides: 1-kestose (1F-b-d-fructofuranosylsucrose) | 470-69-9 | 2.1 ± 1.2 | |
| $F_2$ |  |  | Inulobiose | 9005-80-5 | 2.5 ± 1.5 | |
| $GF_3$ | Trifructooligosaccharide | Nystose | neokestose (6G-b-d-fructofuranosylsucrose); | 13133-07-8 | 3.15 ± 0.3 | 82-91% |

TABLE 3-continued

Oligofructose content of different inulin preparations (including guide to oligofructose terminology). The relative concentrations of the oligofructose has been determined at the Australian Proteome Analysis Facility.

| Short Name | General name | Names (a) | | Names (b) | CAS | Relative conc. (%) |
|---|---|---|---|---|---|---|
| $F_3$ | | | Inulotriose | | 58208-59-6 | 14.9 ± 0.5 |
| $GF_4$ (DP5) | Tetrafructooligosaccharide | Fructofuranosylnystose | | Tetrasaccharides: nystose [1F(1-b-d-fructofuranosyl)2 sucrose], 6G(1-b-d-fructo-furanosyl)2 sucrose and 1F(1-b-d-fructofuranosyl)-6G(1-b-d-fructofuranosyl) sucrose; | | 6.3 ± 0.1 |
| $F_4$ | | | Inulotetrose | | | 16.1 ± 0.8 |
| $GF_5$ (DP6) | Pentafructooligosaccharide | Difructofuranosylnystose | | Pentasaccharides: 1F(1-b-d-fructofuranosyl)3 sucrose, 6G(1-b-d-fructo-furanosyl)3 sucrose, 1F(1-b-d-fructofuranosyl)2-6G (1-b-d-fructofuranosyl) sucrose and 1F(1-b-d-fructofura nosyl)-6G(1-b-d-fructofuranosyl)2 sucrose, | | 7.2 ± 1.8 |
| $F_5$ | | | Inulopentose | | | 9.4 ± 0.5 |
| $GF_6$ (DP7) | Hexafructooligosaccharide | Trifructofuranosylnystose | | Hexasaccharides: 1F(1-b-d-fructofuranosyl)4 sucrose, 6G(1-b-d-fructofuranosyl)4 sucrose, 1F(1-b-d-fructofuranosyl)3-6G(1-b-d-fructofuranosyl) sucrose, 1F(1-b-d-fructofur-anosyl)-6G(1-b-d-fructofuranosyl)3 sucrose and 1F(1-b-d-fructofuranosyl)2-6G(1-b-d-fructofuranosyl)2 sucrose, | | 4 ± 0.8 |
| $F_6$ | | | Inulohexose | | | 1.4 ± 0.2 |
| $GF_7$ (DP8) | Heptafructooligosaccharide | Tetrafructofuranosylnystose | | Heptasaccharides: 1F(1-b-d-fructofuranosyl)5 sucrose | | 0.4 ± 0.2 |
| $F_7$ | | | Inuloheptose | | | 1.7 ± 0.9 |
| $GF_8$ (DP9) | Octafructooligosaccharide | Pentafructofuranosylnystose | | | | 0.4 ± 0.2 |
| $F_8$ | | | Inulooctose | | | 0.5 ± 0.2 |
| $GF_9$ (DP10) | Enneafructooligosaccharide | Hexafructofuranosylnystose | | | | 0.5 ± 0.3    <4% |
| $F_9$ | | | Inuloennea | | | |
| $GF_{10}$ | Decafructooligosaccharide | Pentafructofuranosylnystose | | | | 1 ± 1 |
| $F_{10}$ $GF_{>10}$ | | | Inulodeca | | | |

(a) Tetrahedron: Asymmetry 16 (2005) 33-37
(b) International Journal of Food Science and Technology 2009, 44, 947-952

Table 4 below depicts oligofructose content of a preferred inulin composition that effectively synergize with sulfonylureas.

TABLE 4

Oligofructose (OF) content of inulin Orafti P95 compositions (Analysed at the Australian Proteomic analysis facility). Percentage of each molecular composition of P95

| Comp | OF | AVE | SD |
|---|---|---|---|
| DP2 | F2 | 8.908464 | 0.452405 |
| DP2 | GF | 4.873426 | 1.293211 |
| DP3 | F3 | 14.20397 | 0.486451 |
| DP3 | GF2 | 8.931783 | 0.288154 |
| DP4 | F4 | 16.19856 | 1.982083 |
| DP4 | GF3 | 3.279108 | 0.707716 |
| DP5 | F5 | 8.257493 | 0.791346 |
| DP5 | GF4 | 4.687028 | 0.74578 |

TABLE 4-continued

Oligofructose (OF) content of inulin Orafti P95 compositions
(Analysed at the Australian Proteomic analysis facility).
Percentage of each molecular composition of P95

| Comp | OF | AVE | SD |
|---|---|---|---|
| DP6 | F6 | 0.800649 | 0.085048 |
| DP2 | F2 + GF | 13.78 | 1.745542 |
| DP3 | F3 + GF2 | 23.14 | 0.25201 |
| DP4 | F4 + GF3 | 19.48 | 1.434588 |
| DP5 | F5 + GF4 | 12.94 | 1.532591 |

Table 5 and 6 below depict further examples of defined inulin preparations that effectively synergise with sulfonylureas.

TABLE 5

Comparative content of oligosaccharides of defined inulin preparations including sc FOS and Sensus OFP (Oligofructose Preparation).

| Designation | Component Name | scFOS[1] USA GRAS | Theoretical Special Interest | Orafti P95 | Sensus OFP | Inulin BP/USP | FSANZ Inulin & FOS |
|---|---|---|---|---|---|---|---|
| $GF_2$ | Ketose | | | 5% | ~8% | | |
| $GF_3$ | Nystose | | | 95% majority | ~92% | | |
| $GF_4$ | Fructosylnytose | | | | | | |
| $GF_5$ | | | | | | | |
| $GF_6$ | | | | | | | |
| $GF_7$ | | | | | | | |
| $GF_8$ | | | | | | | |
| $GF_9$ | | | | | | | |
| $GF_{10}$ | | | | | | | |
| $GF_{>10}$ | | | | | | | |

[1] Short-Chain Fructo-oligo saccharides

TABLE 6

Defined inulin preparation with proposed Australian Approved names "AAN".

| Short Hand | AAN | CAS | Relative conc. |
|---|---|---|---|
| $GF_2$ | Difructooligosaccharide (or Kestose) | 470-69-9 | 4-8% |
| $GF_3$ | Trifructooligosaccharide (or Nystose) | 13133-07-8 | 84-95% |
| $GF_4$ | Tetrafructooligosaccharide | | |
| $GF_5$ | Pentafructooligosaccharide | | |
| $GF_6$ | Hexafructooligosaccharide | | |
| $GF_7$ | Heptafructooligosaccharide | | |
| $GF_8$ | Octafructooligosaccharide | | |
| $GF_9$ | Enneafructooligosaccharide | | <5% |
| $GF_{10}$ | Decafructooligosaccharide | | |
| $GF_{>10}$ | | | |

Figure 12:
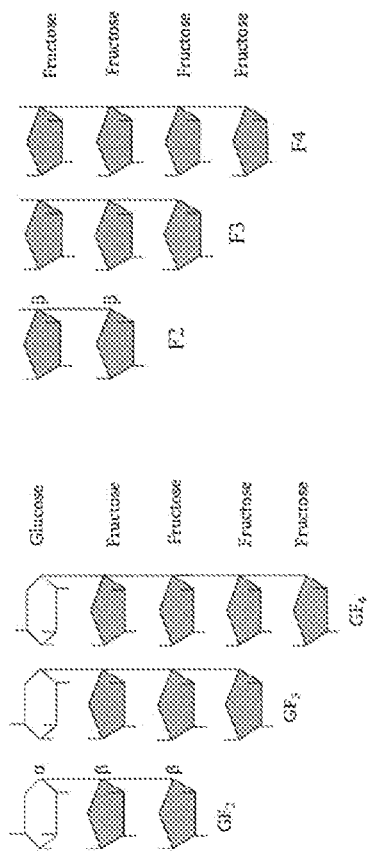
FIG. 12: Schematic diagram showing the relationship between inulin and FOS (left) and the chemical structure of scFOS (right).
Figure 12:
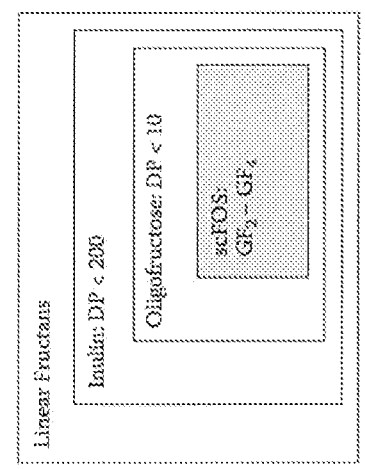

For easy reference, a schematic diagram showing the relationship between inulin and FOS and the chemical structure of scFOS is found in FIG. 12, which is publicly available information and can be found in biochemistry textbooks.

Example 9

Methods of Preparing Inulin for Use in Compositions of the Invention

Inulin preparations with desirable and advantageous DP values and/or with defined OF and/or FOS for use in the compositions of the invention may be obtained commercially. For example the OFP described in Example 8, Sensus OFP is manufactured and distributed by Sensus (Borchwerf 3, 4704 RG Roosendaal, The Netherlands). Commercial inulin preparations such as Sensus OFP are typically isolated as a mixture of oligosaccharides by controlled enzymatic hydrolysis of inulin containing materials, e.g., plant materials, such as, chicory, artichoke and the like. A general overview of the process is shown in the schematic of FIG. 13, which is publicly available on the Sensus website. The manufacturing process has been developed and implemented at full commercial scale for a number of years, in line with EU food processing restrictions and requirements. In general, the process for producing Sensus OFP comprises harvesting chicory roots, extracting the sliced roots with hot water. The purification step removes solids and proteins. Thereafter, demineralisation/decolourisation takes place with known methods in the art. Further purification steps results in the final product which may be supplied as a syrup, or a powder, e.g., spray dried into a powder. A copy of the OFP product specification and the analytical method used for determining the degree of polymerisation of the product can be obtained from Sensus. The product supplied by Sensus can be stored for at least 5 years after production date, if stored in original sealed bags under dry conditions Other native or modified enzymes may be used in any one of the processes described herein using inulin as a substrate. Such native or modified enzymes, include but are not limited to, levansucrase, 1,4-alpha-glucan 6-alpha-glycosyltransferase, 2,1-fructan: 2,1-fructanl-fructosyltransferase, inulinase, beta-fructofuranosidase, sucrose alpha-glucosidase, 2,6-beta-fructan6-levanbiohydrolase, fructanbetafructosidase, fructan beta-(2,1)-fructosidase, inulin fructotransferase (DFA-I-forming), inulin fructotransferase (DFA-II forming). Such enzymes can be readily found by searching a database, e.g., the Brenda enzyme database.

FOS Production: Lower DP Inulins

FOS (inulins with a DP value less than 10 including the preferred forms F2 to F5) for use in the compositions of the invention may be purified from commercial preparations as described above, or similar OF preparations prepared using a method as described above. These processes also utilise native or modified enzymes as described above.

FOS may be produced using any technology described in the art including digestion of substrates (21), as well as enzyme based synthesis from sub-units (22); processes using immobilised enzymes (23) and others that have specifically engineered reaction kinetics as key attributes (24) or use other platforms such as membranes for ordered manufacture (25) may also be used. Use of live organisms to monitor the progression of the reactions as described in (26) is also contemplated.

A number of textbooks describe the production of FOS, the contents of which are incorporated by reference in their entirety (27). Catalytic systems are described, however, such systems require the use of co-factors such as divalent cations (Zn, Mg, Pb, Pt), as well as suitable modification and optimisation of reaction kinetics that will include, time, temperature, pH, substrate or reaction environmental selection.

Synthetic strategies may also be used. Synthetic strategies described range from very basic theory to very advanced systems and include for example; application of strategic approaches including linear glycosylation, convergent block synthesis, single and multi-step strategies, Chemo-selective strategies, solid phase and combined semi-enzymatic methods. In some cases miniature reactors are used. More recent approaches have incorporated both laser and micro-wave mediated systems.

Some of the more advanced systems have also used 'Ionic catch and release methodology (28), HPLC assisted automated systems (29). Systems currently utilised in biofuels manufacture may also be adapted, these can include size reduction, chemical pre-treatment, cell lysis and enzymatic reactions.

Systems including the isolation and utilization of the enzymes that are specifically responsible for the degradation of high DP molecules into specific FOS, and ideally isolation and/or adaption of novel enzymes or organisms that capable of enhanced activity are also contemplated. Such enzymes may be from both prokaryotic and eukaryotic sources, with root vegetable sources being of particular interest. Such enzymes can be readily found by searching an online database, e.g., the Brenda enzyme database.

GF2, GF3 and GF4 may be prepared from sucrose using the enzyme β-fructofuranosidase essentially as described in reference (30) at pages 16 to 17.

It is also contemplated that the Isolation of organisms and or enzymes that are capable of synthesising FOS of the desired DP, for example in a manner similar to dextrans may be used if they are available. Likely sources will include organisms that are known to exude extracellular polysaccharides, for biofilms (31) as well as yeasts (32), other organisms of interest include those that have demonstrable bifidogenic effect (33). Micro-organisms of particular interest will most likely be isolated or derived from extreme environments such as hot (thermophiles), low oxygen (anaerobic or facultative anaerobic), and/or low nutrient environments (for example pseudomonas).

All processes relating to the determination of safety of ingesting FOS are published, e.g., as described in reference (30), the contents of which are incorporated by reference in their entirety.

Example 10

Preparation of Unit Dosage Forms of Inulin Compositions

The inulin preparations described herein, for example, any one of the OFP, FOS, or OF described in Examples 8 and 9, may be supplied directly as a solid or liquid oral dose form or manufactured as a formulation comprising actives and one or more pharmaceutically acceptable carriers, diluents or excipients as part of the manufacture of the dose form. The dose forms include, but are not limited to, liquids (spray, syrup, emulsion, suspension, paste, liquid extract of Chicory or other natural source of inulin, tonic, tincture etc) and including liquid filled capsules; as a semi-solid palatable gel, film, gum or wafer; as a solid form such as pastille, granules, powders, tablets (including chewable, dispersible, effervescent, coated, enteric, hard and soft capsules, etc). Other examples include transdermal, sublingual, injectable, implantable, bolus etc. Processing techniques known in the art maybe used, as well as known pharmaceutically acceptable carriers, diluents or excipients (see generally Remington's Pharmaceutical Sciences, (4) and e.g., references (5) to (20). To prepare such formulations, one or more inulin preparations of the invention described herein, are mixed with a pharmaceutically acceptable carrier or excipient for example, by mixing with physiologically acceptable carriers, excipients, or stabilizers in the form of, e.g., lyophilized powders, slurries, aqueous solutions, or suspensions. Broadly, pharmaceutically acceptable excipients, carriers or stabilizers that are used includes those that provide antioxidant, bulking, capsule lubricants, chelating, coating, colouring, complexing, desiccant, diluent, emollient, emulsification, film forming, flavours, glidant or anti-caking, humectant, sorbent, stiffening, sequestering, suspending, sweetening, tonifying, water repelling, wetting/solubilising etc. and as described in any one of references (4) to (20).

In one example, tabletting is a solid dosage form that allows for preparation of individual and controlled dosage forms and supply with predictable characteristics over a wide range of parameters including:

Dissociation, partitioning and solubility
Release, dissolution and permeation and stability
Commercial and identification parameters
Palatability, dosage compliance, pack-ability etc.
Considerations for designing a tablet inter alia, include:
Quantity of active to be delivered per dose
Desirable attributes of timing and delivery
Stability or reactivity In addition to the general references cited above, further materials, as well as, tablet production and processing techniques and the like are set may be found in Chapter 1 (ref. 19), and Chapters 6, 8, 11 and 13 (ref. 20). For example, suitable excipients, carriers and/or other additives include capsule shells, fillers, desiccants, lubricants and binders and will typically include one or more of cellulose, colloidal anhydrous silica, hypromellose, lactose, lactose-monohydrate, magnesium stearate, maltodextrin, microcrystalline cellulose, povidone, sodium starch glycolate, starch-maize, starch pre-gelatinised, stearic acid or talc.

Other suitable excipients, carriers and/or other additives are provided below by way of non-limiting example. Those listed in bold are preferred.

Acacia
Acesulfame Potassium
Acetic Acid, Glacial
Acetone
Acetyltriethyl Citrate
Agar
Albumin
Alcohol
Alginic Acid
Aliphatic Polyesters
Alitame
Almond Oil
Alpha Tocopherol
Aluminum Hydroxide Adjuvant
Aluminum Oxide
Aluminum Phosphate Adjuvant
Aluminum Stearate
Ammonia Solution
Ammonium Alginate
Ascorbic Acid

| | |
|---|---|
| Ascorbyl Palmitate | Erythorbic Acid |
| Aspartame | Erythritol |
| Attapulgite | Ethyl Acetate |
| Bentonite | Ethyl Lactate |
| Benzalkonium Chloride | Ethyl Maltol |
| Benzethonium Chloride | Ethyl Oleate |
| Benzoic Acid | Ethyl Vanillin |
| Benzyl Alcohol | Ethylcellulose |
| Benzyl Benzoate | Ethylene Glycol |
| Boric Acid | Palmitostearate |
| Bronopol | Ethylene Vinyl Acetate |
| Butylated Hydroxytoluene | Ethylparaben |
| Butylparaben | Fructose |
| Calcium Alginate | Fumaric Acid |
| Calcium Carbonate | Gelatin |
| Calcium Phosphate Dibasic Anhydrous | Glucose, Liquid |
| | Glycerin |
| Calcium Phosphate, Dibasic Dihydrate | Glyceryl Behenate |
| | Glyceryl Monooleate |
| Calcium Phosphate, Tribasic | Glyceryl Monostearate |
| Calcium Stearate | Glyceryl Palmitostearate |
| Calcium Sulfate | Glycofurol |
| Canola Oil | Guar Gum |
| Carbomer | Hectorite |
| Carbon Dioxide | Heptafluoropropane (HFC) |
| Carboxymethylcellulose Calcium | Hexetidine |
| | Hydrocarbons (HC) |
| Carboxymethylcellulose Sodium | Hydrochloric Acid |
| | Hydroxyethyl Cellulose |
| Carrageenan | Hydroxyethylmethyl Cellulose |
| Castor Oil | Hydroxypropyl Cellulose |
| Castor Oil, Hydrogenated | Hydroxypropyl Cellulose, Low-substituted |
| Cellulose, Microcrystalline | |
| Cellulose, Powdered | Hydroxypropyl Starch |
| Cellulose, Silicified Microcrystalline | Hypromellose |
| | Hypromellose Acetate Succinate |
| Cellulose Acetate | |
| Cellulose Acetate Phthalate | Hypromellose Phthalate |
| Ceratonia | Imidurea |
| Cetostearyl Alcohol | Inulin |
| Cetrimide | Iron Oxides |
| Cetyl Alcohol | Isomalt |
| Cetylpyridinium Chloride | Isopropyl Alcohol |
| Chitosan | Isopropyl Myristate |
| Chlorhexidine | Isopropyl Palmitate |
| Chlorobutanol | Kaolin |
| Chlorocresol | Lactic Acid |
| Chlorodifluoroethane (HCFC) | Lactitol |
| Chlorofluorocarbons (CFC) | Lactose, Anhydrous |
| Chloroxylenol | Lactose, Monohydrate |
| Cholesterol | Lactose, Spray-Dried |
| Citric Acid Monohydrate | Lanolin |
| Colloidal Silicon Dioxide | Lanolin Alcohols |
| Coloring Agents | Lanolin Hydrous |
| Copovidone | Lauric Acid |
| Corn Oil | Lecithin |
| Cottonseed Oil | Leucine |
| Cresol | Linoleic Acid |
| Croscarmellose Sodium | Macrogol 15 Hydroxystearate |
| Crospovidone | Magnesium Aluminum Silicate |
| Cyclodextrins | Magnesium Carbonate |
| Cyclomethicone | Magnesium Oxide |
| Denatonium Benzoate | Magnesium Silicate |
| Dextrates | Magnesium Stearate |
| Dextrin | Magnesium Trisilicate |
| Dextrose | Malic Acid |
| Dibutyl Phthalate | Maltitol |
| Dibutyl Sebacate | Maltitol Solution |
| Diethanolamine | Maltodextrin |
| Diethyl Phthalate | Maltol |
| Difluoroethane (HFC) | Maltose |
| Dimethicone | Mannitol |
| Dimethyl Ether | Medium-chain Triglycerides |
| Dimethyl Phthalate | Meglumine |
| Dimethyl Sulfoxide | Menthol |
| Dimethylacetamide | Methylcellulose |
| Disodium Edetate | Methylparaben |
| Docusate Sodium | Mineral Oil |
| Edetic Acid | Light Mineral Oil and Lanolin |

-continued

Alcohols
Monoethanolamine
Monosodium Glutamate
Monothioglycerol
Myristic Acid
Neohesperidin Dihydrochalcone
Nitrogen
Nitrous Oxide
Octyldodecanol
Oleic Acid Oleyl Alcohol
Olive Oil
Palmitic Acid
Paraffin
Peanut Oil
Pectin
Petrolatum
Petrolatum and Lanolin Alcohols
Phenol
Phenoxyethanol
Phenylethyl Alcohol
Phenylmercuric Acetate
Phenylmercuric Borate
Phenylmercuric Nitrate
Phosphoric Acid
Polacrilin Potassium
Poloxamer
Polycarbophil
Polydextrose
Polyethylene Glycol
Polyethylene Oxide
Polymethacrylates
Poly(methyl vinyl ether/maleic anhydride)
Polyoxyethylene Alkyl Ethers
Polyoxyethylene Castor Oil Derivatives
Polyoxyethylene Sorbitan Fatty Acid Esters
Polyoxyethylene Stearates
Polyvinyl Acetate Phthalate
Polyvinyl Alcohol
Potassium Alginate
Potassium Benzoate
Potassium Bicarbonate
Potassium Chloride
Potassium Citrate
Potassium Hydroxide
Potassium Metabisulfite
Potassium Sorbate
Povidone
Propionic Acid
Propyl Gallate
Propylene Carbonate
Propylene Glycol
Propylene Glycol Alginate
Propylparaben
2-Pyrrolidone
Raffinose
Saccharin
Saccharin Sodium
Saponite
Sesame Oil
Shellac
Simethicone
Sodium Acetate
Sodium Alginate
Sodium Ascorbate
Sodium Benzoate
Sodium Bicarbonate
Sodium Borate
Sodium Chloride
Sodium Citrate Dihydrate
Sodium Cyclamate
Sodium Hyaluronate
Sodium Hydroxide
Sodium Lactate
Sodium Lauryl Sulfate
Sodium Metabisulfite
Sodium Phosphate -continued Dibasic Sodium Phosphate
Monobasic Sodium Propionate
Sodium Starch Glycolate
Sodium Stearyl Fumarate
Sodium Sulfite
Sorbic Acid
Sorbitan Esters (Sorbitan Fatty Acid Esters)
Sorbitol
Soybean Oil
Starch
Starch Pregelatinized Starch
Sterilizable Maize
Stearic Acid
Stearyl Alcohol
Sucralose
Sucrose
Sugar, Compressible
Sugar, Confectioner's
Sugar Spheres
Sulfobutylether b-Cyclodextrin
Sulfuric Acid
Sunflower Oil
Suppository Bases, Hard Fat
Talc
Tartaric Acid
Tetrafluoroethane (HFC)
Thaumatin
Thimerosal
Thymol
Titanium Dioxide
Tragacanth
Trehalose
Triacetin
Tributyl Citrate
Triethanolamine
Triethyl Citrate
Vanillin
Vegetable Oil, Hydrogenated
Water
Wax, Anionic Emulsifying
Wax, Carnauba
Wax, Cetyl Esters
Wax, Microcrystalline
Wax, Nonionic Emulsifying
Wax, White
Wax, Yellow
Xanthan Gum
Xylitol
Zein
Zinc Acetate
Zinc Stearate

Tabletting Process:

By way of non-limiting example, tablets according the following schedule were produced:

| Raw materials | Claim/Label | mg/tablet | Batch |
|---|---|---|---|
| Inulin powder** | 1500 | 1500 mg | 702.33 g |
| Sodium starch glycollate | | 63 mg | 29.5 g |
| Magnesium stearate | | 8 mg | 3.75 g |
| Total tablet weight | | 1571 mg | |

**The inulin powder in the above schedule includes one of the inulin preparations of the invention, for example, any one of the OFP, FOS, or OF described in Examples 8 and 9. Tablets including Sensus brand OFP were prepared.

It is noted that both sodium starch glycolate and magnesium stearate are routinely included as excipients in tablets formulated for management of type 2 diabetes; including those with sulfonylurea as an active ingredient. There are no reported interactions between Inulin (or fructo oligosaccharides) and any of the proposed excipients, each of which are included in a number of pharmacopeia and are recognised as excipient ingredients.

Sodium Starch Glycolate 63 mg (4% w/w)

There are a number of different variants of cross linked Sodium Starch Glycolate, each of which are prepared from potato starch. It is used as a disintergrant in tablet and capsule manufacture. This excipient is considered to be chemically stable and is chemically incompatible with ascorbic acid. There are reported pharmacological interactions between sodium starch glycolate and glycopeptide antibiotics and basic (alkaline) drugs. References (11), (13), (14) and (15) contain additional pharmacopeial data pertaining to this substance. The concentration used is considered to be optimal with typical concentrations quoted as being between 2 and 8%.

Magnesium Stearate 8 mg (0.5% w/w)

Magnesium stearate is a compound that acts as a lubricant in tabletting and encapsulation regimes comprised of solid organic acids (stearate and Palmitate) and magnesium. The specific surface area is an important characteristic in the suitability to various dose forms and must be determined for batch to batch consistency. It has the molecular formula $C_{36}H_{70}MgO_4$ (5911.34 and the structural formula $[CH_3(CH_2)_{16}COO]_2Mg$. While chemically stable it is considered incompatible with strong acids, strong alkalies and iron salts. It cannot be used in conjunction with products containing aspirin, some vitamins and most alkaloid salts. References (11), (13), (14) and (15) contains additional Pharmacopeial data about this substance. The concentration quoted is considered to be appropriate, with typical concentrations between 0.25 and 5% w/w.

An example of the tabletting process is described. Typically doses are manufactured using the following regimes.

Materials preparation
Dose form assembly
Quality control and packaging

Materials preparation initially includes inspecting each of the substances for suitability for intended use and quantitatively dispensing known amounts of each of the excipients. This is followed by screening, a process whereby ingredients are passed through a physical screen or past a screening device that identifies and/or removes particulates that are not conducive to preparing a uniform dosage form. Screening can be manual, semi-automatic or fully automatic process. Other control steps such as metal detection or sampling and QC analysis of starting materials can also be employed at this stage.

Materials preparation can also include milling, a process whereby products are reduced or standardised in size; typically, this may be undertaken in conjunction with other processes, for individual ingredients and/or for blends. Milling helps to ensure uniformity, and may be applied in a variable manner, depending on the physical nature of the ingredients. Milling is achieved using any known process in the art and includes the use of equipment including choppers, hammer mills, grinder, vertical impact, high shear, ball mills (etc).

To prepare the active ingredient for division into discrete dosage forms, blending may be used. Blending may be performed at sub-batch, batch or as a continuous process and will typically employ the physical mixing and agitation of known amounts of ingredient materials. In commercial preparations the products are typically automated, and can include wet and dry blending.

Dry blending typically applies a turbulent process, such as tumbling, ribbon blending, vibration and similar regimes. The nature duration of mixing will be dependent on the flow characteristics of the materials, the range in particulate size, the hydration of the materials, the specific absorption profiles of the formulations and the prevailing material and environmental conditions.

Often pre-blending or pre-compression activities such as 'granulation' are also employed. Granules can be prepared using methods such as wet or dry granulation, fluid bed granulation, moisture activated dry granulation, spray drying and the like. Fluids can include for example; water, tinctures or solvents, steam or melted components. Where moisture or fluids are employed, they are typically removed from the granulated mass by means of heat, vacuum, hot air, dehydration, desiccation, setting, aging and the like.

Following ingredients preparation, tablets are compressed into their dosage form. Typically this process is highly automated; using 'presses' that compress measured amounts of granules or powder between 'dies'. These die comprise two complementary pieces that meet under pressure and thereby compress the preparation into tablets of pre-defined size, shape, hardness and friability. Pneumatic, hydrolytic and mechanical compression can be used.

Typically compressed tablets are de-dusted by tumbling, brushing, vacuum or the like.

Following compression, and if merited by the design of the dose form tablets may be coated using a suitable coating substance, this can be for the purpose of colouring, smoothing, modifying the taste, stability or digestion characteristics of the solid dosage form. De-dusted tablet 'cores' are tumbled and then sprayed or otherwise coated with a liquid or liquefied coating material that is applied evenly across the outer-surface of the tablet cores, usually in several layers or as an extended process, and then allowed to dry.

Tablets or coated tablets are inspected either manually or electronically for defects. The content, physical characteristics, and predictable biochemical attributes are assessed using assay, evaluation and related QC.

Examples of the Physical Parameters tested, e.g., for the tablets produced according to the above Schedule are as follows:

| Test | Acceptable Range | Ref Method(s) |
| --- | --- | --- |
| Colour & Appearance | (colour) | |
| Shape | (describe) | |
| Dimensions | (quantity) | |
| Average Mass/ | 1571 mg | *BP Appendix XII C |
| Uniformity of mass | +/−5% = 1492.45 to 1649.55 mg | Weigh individually 20 units taken at random and determine the average |
| | +/−10% = 1413.9 to 1728.1 mg | mass. NMT 2 of the individual masses deviate from the average mass by more than 5% and none deviates by more than 10%. |
| Dissolution | Not more than 30 minutes | *BP Appendix XII B Conventional release solid dosage forms |

-continued

| Test | Acceptable Range | Ref Method(s) |
|---|---|---|
| Friability | Not more than 1% weight loss | *BP Appendix XVII G Uncoated Tablets |
| Breaking Force | (to be determined) Max and Min newtons of 6 tablets | **USP/*BP |
| Uniformity of Dosage from | Content Uniformity of 30 tablets | *BP Appendix XII C |

*BP-British Pharmacopeia (ref. 11).
**USP-US Pharmacopeia (ref. 13).

Bulk tablets are then packed into suitable matching that can include, blisters, bottles, dispensers etc. Any packaging and labelling may be used provided it is suitable for maintaining the identity, integrity and efficacy of the products.

Example 11

Inulin Containing Unit Dosage Formulations of Sulfonylureas

Unit dosage forms of any one of the inulin preparations of the invention and sulfonylurea may be easily derived from the information provided in the tables 7 to 12 below, which provide, by way of non-limiting examples only, the various quantities and relative proportions of inulins and sulfonylureas. The information provided in the tables is approximate and it will be understood from the data provided that unit dosage forms may contain quantities of inulins and sulfonylurea so as to achieve effective treatment when administered to the patient from one to several time per day. Desirably, unit dosage forms, such as tablets, capsules or similar, are formulated so as to allow e.g., 2 to 4 unit dosage forms to be taken 2 to 3 times daily. Thus, the unit dosage form may contain a sulfonylurea in the amount from about 0.5 to about 2000 mg, or as described herein above. The amount of sulfonylurea in the unit dosage form may vary with the type of sulfonylurea used and treatment regimen required, both of which can be easily determined by a medical practitioner. The absolute quantity of inulin per dosage form will depend on the inulin used and, if being compressed into a tablet dosage form, on compressibility of inulin so as to provide for an acceptable size tablet. The quantity of inulin may range from about 5 mg to about 50 grams per dosage form, or as described herein above. A suitable dosage form may be, for example, a tablet comprising 500-1000 mg of inulin and 1 to 30 mg sulfonylurea (but may be higher depending on the type of sulfonylurea used). Three to four such dosage forms may be taken 3 times daily to achieve effective treatment (e.g. lowering of blood glucose level). The quantity of each ingredient may be greater if compressibility of inulin used allows it in order to achieve a suitably sized dosage form.

TABLE 7

Molecular characteristics of selected sulfonylureas and sugar monomers

| | | gr/mole | | mmole |
|---|---|---|---|---|
| $C_6H_{12}O_6$ | Glucose Mw | 180.15588 | | |
| $C_6H_{12}O_6$ | Fructose Mw | 180.15588 | | |
| $C_{23}H_{28}ClN_3O_5S$ | Glibenclamide | 494.004 | 15 mg daily (3x) = | 0.030364 |
| $C_{15}H_{21}N_3O_3S$ | Gliclazide | 323.412 | 30 mg daily (1x) = | 0.092761 |
| $C_{24}H_{34}N_4O_5S$ | Glimepiride | 490.617 | 4 mg daily (1x) = | 0.008153 |
| $C_{21}H_{27}N_5O_4S$ | Glipizide | 445.536 | 15 mg daily (3x) = | 0.033667 |

TABLE 8

Inulin/Glibenclamide

| | 12 gram/15 mg per day | | | Ratio (w/w) | |
|---|---|---|---|---|---|
| | MW gr/mole | Lowest (mg)* | Highest (mg)* | Inulin/Glib Lowest | Inulin/Glib Highest |
| F3 | 540.47 | 2532 | 3336 | 169 | 222 |
| GF2 | 540.47 | 168 | 324 | 11 | 22 |
| F4 | 720.62 | 2052 | 2760 | 137 | 184 |
| GF3 | 720.62 | 468 | 756 | 31 | 50 |
| F5 | 900.78 | 1044 | 1572 | 70 | 105 |
| GF4 | 900.78 | 660 | 1140 | 44 | 76 |
| F6 | 1080.94 | 660 | 1044 | 44 | 70 |
| GF5 | 1080.94 | 708 | 1008 | 47 | 67 |
| F3 + F4 + F5 = | | 5628 | 7668 | 375 | 511 |

| | 15 gram/15 mg per day | | | Ratio (w/w) | |
|---|---|---|---|---|---|
| | MW gr/mole | Lowest (mg)* | Highest (mg)* | Inulin/Glib Lowest | Inulin/Glib Highest |
| F3 | 540.47 | 3165 | 4170 | 211 | 278 |
| GF2 | 540.47 | 210 | 405 | 14 | 27 |
| F4 | 720.62 | 2565 | 3450 | 171 | 230 |
| GF3 | 720.62 | 585 | 945 | 39 | 63 |
| F5 | 900.78 | 1305 | 1965 | 87 | 131 |
| GF4 | 900.78 | 825 | 1425 | 55 | 95 |
| F6 | 1080.94 | 825 | 1305 | 55 | 87 |
| GF5 | 1080.94 | 885 | 1260 | 59 | 84 |
| F3 + F4 + F5 = | | 7035 | 9585 | 469 | 639 |

TABLE 9

Inulin/Gliclazide 12 gram/30 mg per day

| | MW gr/mole | Lowest (mg)* | Highest (mg)* | Inulin/Glic Lowest | Inulin/Glic Highest |
|---|---|---|---|---|---|
| F3 | 540.47 | 2532 | 3336 | 84 | 111 |
| GF2 | 540.47 | 168 | 324 | 6 | 11 |
| F4 | 720.62 | 2052 | 2760 | 68 | 92 |
| GF3 | 720.62 | 468 | 756 | 16 | 25 |
| F5 | 900.78 | 1044 | 1572 | 35 | 52 |
| GF4 | 900.78 | 660 | 1140 | 22 | 38 |
| F6 | 1080.94 | 660 | 1044 | 22 | 35 |
| GF5 | 1080.94 | 708 | 1008 | 24 | 34 |
| F3 + F4 + F5 = | | 5628 | 7668 | 188 | 256 |

15 gram/30 mg per day

| | MW gr/mole | Lowest (mg)* | Highest (mg)* | Inulin/Glic Lowest | Inulin/Glic Highest |
|---|---|---|---|---|---|
| F3 | 540.47 | 3165 | 4170 | 105.5 | 139 |
| GF2 | 540.47 | 210 | 405 | 7 | 13.5 |
| F4 | 720.62 | 2565 | 3450 | 85.5 | 115 |
| GF3 | 720.62 | 585 | 945 | 19.5 | 31.5 |
| F5 | 900.78 | 1305 | 1965 | 43.5 | 65.5 |
| GF4 | 900.78 | 825 | 1425 | 27.5 | 47.5 |
| F6 | 1080.94 | 825 | 1305 | 27.5 | 43.5 |
| GF5 | 1080.94 | 885 | 1260 | 29.5 | 42 |
| F3 + F4 + F5 = | | 7035 | 9585 | 235 | 320 |

TABLE 10

Inulin/Glimepiride 12 gram/4 mg per day

| | MW gr/mole | Lowest (mg)* | Highest (mg)* | Inulin/Glim Lowest | Inulin/Glim Highest |
|---|---|---|---|---|---|
| F3 | 540.468 | 2532 | 3336 | 633 | 834 |
| GF2 | 540.468 | 168 | 324 | 42 | 81 |
| F4 | 720.624 | 2052 | 2760 | 513 | 690 |
| GF3 | 720.624 | 468 | 756 | 117 | 189 |
| F5 | 900.779 | 1044 | 1572 | 261 | 393 |
| GF4 | 900.779 | 660 | 1140 | 165 | 285 |
| F6 | 1080.935 | 660 | 1044 | 165 | 261 |
| GF5 | 1080.935 | 708 | 1008 | 177 | 252 |
| F3 + F4 + F5 = | | 5628 | 7668 | 1407 | 1917 |

15 gram/4 mg per day

| | MW gr/mole | Lowest (mg)* | Highest (mg)* | Inulin/Glim Lowest | Inulin/Glim Highest |
|---|---|---|---|---|---|
| F3 | 540.468 | 3165 | 4170 | 791 | 1043 |
| GF2 | 540.468 | 210 | 405 | 53 | 101 |
| F4 | 720.624 | 2565 | 3450 | 641 | 863 |
| GF3 | 720.624 | 585 | 945 | 146 | 236 |
| F5 | 900.779 | 1305 | 1965 | 326 | 491 |
| GF4 | 900.779 | 825 | 1425 | 206 | 356 |
| F6 | 1080.935 | 825 | 1305 | 206 | 326 |
| GF5 | 1080.935 | 885 | 1260 | 221 | 315 |
| F3 + F4 + F5 = | | 7035 | 9585 | 1758.75 | 2396.25 |

TABLE 11

Inulin/Glipizide 12 gram/15 mg per day

| | MW gr/mole | Lowest (mg)* | Highest (mg)* | Inulin/Glip Lowest | Inulin/Glip Highest |
|---|---|---|---|---|---|
| F3 | 540.47 | 2532 | 3336 | 169 | 222 |
| GF2 | 540.47 | 168 | 324 | 11 | 22 |
| F4 | 720.62 | 2052 | 2760 | 137 | 184 |
| GF3 | 720.62 | 468 | 756 | 31 | 50 |
| F5 | 900.78 | 1044 | 1572 | 70 | 105 |
| GF4 | 900.78 | 660 | 1140 | 44 | 76 |
| F6 | 1080.94 | 660 | 1044 | 44 | 70 |
| GF5 | 1080.94 | 708 | 1008 | 47 | 67 |
| F3 + F4 + F5 = | | 5628 | 7668 | 375.2 | 511.2 |

15 gram/15 mg per day

| | MW gr/mole | Lowest (mg)* | Highest (mg)* | Inulin/Glip Lowest | Inulin/Glip Highest |
|---|---|---|---|---|---|
| F3 | 540.47 | 3165 | 4170 | 211 | 278 |
| GF2 | 540.47 | 210 | 405 | 14 | 27 |
| F4 | 720.62 | 2565 | 3450 | 171 | 230 |
| GF3 | 720.62 | 585 | 945 | 39 | 63 |
| F5 | 900.78 | 1305 | 1965 | 87 | 131 |
| GF4 | 900.78 | 825 | 1425 | 55 | 95 |
| F6 | 1080.94 | 825 | 1305 | 55 | 87 |
| GF5 | 1080.94 | 885 | 1260 | 59 | 84 |
| F3 + F4 + F5 = | | 7035 | 9585 | 469 | 639 |

*The "lowest (mg)" and "highest (mg)" values are based on the variable content of the specified OF in the inulin preparations.

TABLE 12

Summary of useful sulfonylurea/inulin weight and molar ratios for selected formulations

| Composition | Weight Ratio | Molar Ratio |
|---|---|---|
| Glibenclimide:Inulin | 1:375 to 1:639 | 1:286 to 1:484 |
| Gliclazide:Inulin | 1:188 to 1:320 | 1:94 to 1:158 |
| Glimepiride:Inulin | 1:1407 to 1:2396 | 1:1066 to 1:1801 |
| Glipizide:Inulin | 1:375-1:639 | 1:258-1:436 |

A person skilled in the art will understand that the above ratio will change depending on the form of inulin used, as the above molar ratios are calculated using Sensus OFP. Accordingly, the ratios will differ with higher efficacy inulin forms and discrete pure oligos. A person skilled in the art will understand how to calculate such ratios based on the dosage used of each component.

Example 12

Clinical Trial

Clinical trials are performed according to the parameters described herein to assess the efficacy of different doses of inulin and/or FOS preparations on glycemic control in patients with T2DM. The inulin and/or FOS preparation may be any preparation of inulin and/or FOS including unit dosage forms suitable for this purpose, e.g., as described in any one of the Examples, referred to as "inulin-preparation". At least one clinical trial including a purified food grade inulin-preparation that comprises the OF content as described in Table 4 or Table 6 is used. In another clinical trial, ORAFTI P95 is used. In another clinical trial Sensus OFP is used. Briefly, the clinical trial includes individuals who are exclusively treated with second generation sulfonylurea (preferably with glibenclamide, gliclazide, glimepiride and glipizide) monotherapy and have uncontrolled blood glucose levels. The effect of the inulin-preparation on end-point parameters such as (i) fasting blood glucose levels (FGL), (ii) haemoglobin A1c (HA1c) and (iii) weight is assessed. Other diabetes related markers such as (iv) post prandial glucose levels (PPGL), (v) fructoseamine, (vi) glucagon-like peptide 1 (GLP-1) and (vii) blood insulin levels is assessed. Variables such as the number of hypoglycaemic episodes, patient's activity status, satiety, patient's quality of life, stool microflora, circulating lipopolysaccharide (LPS), haematology, biochemistry, lipid profiles, erythrocyte sedimentation rate, C reactive protein, echocardiography and ophthalmic conditions of the patients is also assessed. Pharmacokinetic and pharmacodynamic of the inulin preparation and sulfonylurea, as well as, safety and tolerability of combination of the inulin preparation and sulfonylurea is also assessed. The effect of addition of the inulin preparation on absorption, distribution, metabolism and excretion of sulfonylurea is determined.

Four treatment groups consisting of 9 patients per group (total 36 patients) are to be enrolled in this trial. For each group, patients are randomized depending on their gender, age, body mass index and genetic background. Patients with baseline FGL of above 7 mmol/L are recruited. Group 1 is the control group and are given sulfonylurea anti-diabetics for the entire trial. Group 2 consists of patients on sulfonylurea and taking the inulin preparation at 3×1.5 grams (4.5 grams/day) doses. Group 3 consists patients on sulfonylurea and taking inulin preparation at 6×1.5 grams (9 grams/day) doses. Group 4 consists of patients on sulfonylurea and taking inulin preparation at 9×1.5 grams (13.5 grams/day) doses. Initially each group is treated with the recommended doses. In the event that after 12 weeks of treatment, any patient showing no improvement on his/her FGL then the inulin preparation dose is increased by 4.5 grams/day increments for the following 12 weeks (Table 9). The maximum daily doses of inulin preparation used in this trial are below the regulatory authorities (e.g. FSANZ and TGA, FDA) recommended average maximum daily doses for consumption by healthy individuals (41grams/day). This treatment regime tests several doses and preparations of inulin and/or FOS on various patient populations.

Although the invention has been described with reference to specific embodiments it will be understood that variations and modifications in keeping with the principles and spirit of the invention described are also encompassed.

REFERENCES

1. Bornet F R J (1994) Undigestible sugars in food products. American Journal of Clinical Nutrition 59, 763S-769S.
2. De Leenheer L (1996) Production and use of inulin: Industrial reality with a Promising future. In Carbohydrates as Organic Raw Materials III, pp. 67-92 [H Van Bekkum, H Roper and A G J Voragen, editors]. New York, N.Y.: VCH Publishers Inc.
3. Csanadi, Z S and Sisak C S (2008) Production of short chain fructooligosaccharides. Hungarian Journal of Industrial Chemistry, Vol 36(1-2), pp. 23-26
4. Remington's Pharmaceutical Sciences (2000), *Mack Publishing Company*, Easton, Pa., USA 20.sup.th Edition, 2000
5. Hardman, et al. (2001) Goodman and Gilman's The Pharmacological Basis of Therapeutics, McGraw-Hill, New York, N.Y.
6. Gennaro (2000) Remington: The Science and Practice of Pharmacy, Lippincott, Williams, and Wilkins, New York, N.Y.
7. Avis, et al. (eds.) (1993) Pharmaceutical Dosage Forms: Parenteral Medications, Marcel Dekker, NY
8. Lieberman, et al. (eds.) (1990) Pharmaceutical Dosage Forms: Tablets, Marcel Dekker, NY
9. Lieberman, et al. (eds.) (1990) Pharmaceutical Dosage Forms: Disperse Systems, Marcel Dekker, NY
10. Weiner and Kotkoskie (2000) Excipient Toxicity and Safety, Marcel Dekker, Inc., New York, N.Y.
11. British Pharmacopeia (2011), The Stationary Office on behalf of the Medicines and Healthcare products Regulatory Agency (MHRA).
12. Rowe, at al. (eds.) (2006) Handbook of Pharmaceutical Excipients, Buttler & Tanner, Frome Somerset, Great Britain.
13. United States Pharmacopeia, (2012), US Pharmacopeial Convention.
14. Japanese Pharmacopeia, Fifteenth Edition (2006), Evaluation and Licensing Division, Pharmaceutical and Food Safety Bureau, Ministry of Health, Labour and Welfare.
15. Sweetman S (ed.)(2007), Martindale: The Complete Drug Reference, Pharmaceutical Press, London

TABLE 13

Combination trial dosage regimen.

| | | Treatments | | | |
|---|---|---|---|---|---|
| | | Dosage of inulin and/or FOS preparation (grams/day) | | | |
| Patients Groups | Sulfonylurea At recommended dosage | At the start of week 12 | At the start of week 28 | At the start of week 44 | Max dosage |
| 1 | Any second generation | 0 | 0 | 0 | 0 |
| 2 | Any second generation | 4.5 | 4.5-9 | 4.5-13.5 | 13.5 |
| 3 | Any second generation | 9 | 9-13.5 | 9-18 | 18 |
| 4 | Any second generation | 13.5 | 13.5-18 | 13.5-22.5 | 22.5 |

16. Maryadele et al. (eds.)(2006), The Merck Index, Merck Research Laboratories, Merch & Co., Inc. NJ, USA. 17. Katdare and Chaubal (eds.)(2006), Excipient Development for Pharmaceutical, Biotechnology, and Drug Delivery Systems, Informa Health Care, USA
18. Niazi (ed)(2007), Handbook of Preformulation, Chemical, biological, and Botanical Drugs, Informa Health Care, USA
19. Parikh (ed)(2010), Handbook of Pharmaceutical Granulation Technology, Informa
Healthcare, USA
20. First Edition (2009), Developing Solid Oral Dosage Forms: Pharmaceutical Theory and Practice, Elsevier Inc., USA
21. Ichikawa et al. (1992), Analytical Biochemistry 202: pp 215-238
22. Singh and Singh (2010), Food Technol. Biotechnol. 48 (4): pp 435-450.
23. Nguyen et al. (2011), Process Biochemistry 46: pp 298-303.
24. Siebel et al. (2009), Adv. Biochem Engin/Biotechnol 54, Extending Synthetic Routes for Oligosaccharides by Enzyme, Substrate and Reaction Engineering.
25. Olano-Martin et al. (2001), Journal of Food Science, 66 (7): pp 966-971.
26. Kaplan and Hutkins (2012), Appl. Environ. Microbiol. 66(6):2682-2684.
27. Polaina and MacCabe (eds.)(2007), Industrial Enzymes, Structure, Function and Applications, Springer, The Netherlands.
28. Tran et al. (2011), Chem. Commun., 47: pp 4526-4528.
29. Ganesh et al. (2012), Organic Letters, 14(12): pp 3036-3039.
30. Generally Recognised as Safe Notification for Short-Chain Fructooligosaccharide (2000), prepared for GTC Nutrition Company Golden Colorado, Prepared by Environ International Corporation Arlington, Va.
35. Harrah et al. (2006), Prokaryotes, 1: pp 766-776.
36. Pavlova et al. (2009), Folia Microbiol. 54 (4): pp 343-348.
37. Meyer and Stasse-Wolthuis (2009), European Journal of Clinical Nutrition, 63: pp 1277-1289.

The invention claimed is:

1. Improved synergistic composition comprising inulin having Degree of Polymerization (DP) below about 25 and a sulfonylurea and/or a derivative and/or a metabolite thereof, and/or a sulfonamide and/or a derivative and/or a metabolite thereof, or a combination thereof, for the treatment of diabetes, or wherein the diabetes is type-2 diabetes mellitus, optionally in combination with one or more excipients.

2. Improved synergistic composition according to claim 1, wherein inulin has a DP in the range of from about 2 to about 23, or in the range from about 2 to about 10, or in the range from about 2 to about 5.

3. Improved synergistic composition according to claim 2, wherein inulin comprises F-F, F-F-F, F-F-F-F and/or F-F-F-F-F, where F represents fructose moieties.

4. Improved synergistic composition according to claim 1, wherein the sulfonylurea is selected from the group consisting of Gliclazide, Glisoxepide, Glibenclamide, Glipizide, Glibornuride, Glimepiride, Gliquidone, Glyclopyrimide, Tolazamide, Tolbutamide, Chlorpropamide, Metahexamide, Carbutamide, Acetohexamide and combinations thereof, or wherein the sulfonamide is selected from Sulfamethoxazole, Sulfisomidine, Sulfacetamide, Sulfadoxine, Dichlorphenamide (DCP) and Dorzolamide.

5. Improved synergistic composition according to claim 1, wherein the composition consists essentially of inulin and sulfonylurea and/or the derivative and/or the metabolite thereof, and/or the sulfonamide and/or the derivative and/or the metabolites thereof, or the combination thereof.

6. Improved synergistic composition according to claim 1, wherein the composition is in a unit dosage form, optionally wherein the unit dosage form is a tablet or capsule.

7. Improved synergistic composition according to claim 6, wherein unit dosage form comprises from about 5 mg to about 50 g of inulin, and
    wherein the unit dosage form comprises from about 0.5 mg to about 2000 mg of sulfonylurea, and/or the derivative and/or the metabolite thereof, and/or the sulfonamide and/or the derivative and/or the metabolite thereof, or the combination thereof.

8. Method of delaying onset of diabetes or therapeutic treatment of diabetes, wherein the diabetes is type-2 diabetes mellitus, said method comprising the administration of inulin having a DP below about 25 in combination with a sulfonylurea and/or a derivative and/or a metabolites thereof, and/or a sulfonamide and/or a derivative and/or a metabolite thereof, or a combination thereof, to a subject requiring such treatment of inulin in an amount and for a time sufficient to reduce, regulate or normalize blood glucose concentration.

9. Method according to claim 8, wherein the inulin improves efficacy of sulfonylurea and/or the derivative and/or the metabolite thereof, and/or the sulfonamide and/or the derivative and/or the metabolite thereof, or the combination thereof, wherein the improved efficacy results in a reduction in required dosage of sulfonylurea and/or the derivative and/or the metabolite thereof, and/or the sulfonamide and/or the derivative and/or the metabolite thereof, or the combination thereof, or results in no dosage increase of the sulfonylurea and/or the derivative and/or the metabolite thereof, and/or the sulfonamide and/or the derivative and/or the metabolite thereof, or the combination thereof, administered to the subject with diabetes, wherein diabetes is type 2 diabetes mellitus.

10. Method of treating hyperglycemia comprising the administration to a subject requiring such treatment of inulin having a DP below about 25 and a sulfonylurea and/or a derivative and/or a metabolite thereof, and/or a sulfonamide a derivative and/or a metabolite thereof, or a combination thereof, in the amount and for a-time sufficient to reduce, regulate or normalize blood glucose concentration.

11. The method according to claim 8, wherein inulin is administered to the subject simultaneously or sequentially, in any order, with the sulfonylurea and/or the derivative and/or the metabolite thereof, and/or the sulfonamide and/or derivative and/or metabolite thereof, or the combination thereof.

12. The method according to claim 9, wherein inulin is administered to the subject simultaneously or sequentially, in any order, with the sulfonylurea and/or the derivative and/or the metabolite thereof, and/or the sulfonamide and/or the derivative and/or the metabolite thereof, or the combination thereof.

13. The method according to claim 10, wherein inulin is administered to the subject simultaneously or sequentially, in any order, with the sulfonylurea and/or the derivative and/or the metabolite thereof, and/or the sulfonamide and/or the derivative and/or the metabolite thereof, or the combination thereof.

14. Method of delaying onset of diabetes or therapeutic treatment of diabetes, or wherein the diabetes is type-2 diabetes mellitus, the method comprising the administration to a subject requiring such treatment of an improved synergistic composition of claim 2.

15. Method of delaying onset of diabetes or therapeutic treatment of diabetes, or wherein the diabetes is type-2 diabetes mellitus, the method comprising the administration to a subject requiring such treatment of an improved synergistic composition of claim 3.

16. Method of delaying onset of diabetes or therapeutic treatment of diabetes, or wherein the diabetes is type-2 diabetes mellitus, the method comprising the administration to a subject requiring such treatment of an improved synergistic composition of claim 4.

17. Method of delaying onset of diabetes or therapeutic treatment of diabetes, or wherein the diabetes is type-2 diabetes mellitus, the method comprising the administration to a subject requiring such treatment of an improved synergistic composition of claim 5.

18. Method of delaying onset of diabetes or therapeutic treatment of diabetes, or wherein the diabetes is type-2 diabetes mellitus, the method comprising the administration to a subject requiring such treatment of an improved synergistic composition of claim 6.

19. Method of delaying onset of diabetes or therapeutic treatment of diabetes, or wherein the diabetes is type-2 diabetes mellitus, the method comprising the administration to a subject requiring such treatment of an improved synergistic composition of claim 7.

20. Method according to claim 8, wherein the inulin is administered to the subject in the amount from about 5 mg to about 50g.

21. Method according to claim 8, wherein the sulfonylurea, and/or the sulfonamide and/or derivatives and/or metabolites thereof, or combinations thereof is administered to the subject in the amount from about 0.5 mg to about 2000 mg.

22. Method according to 8, wherein the sulfonylurea is selected from the group consisting of Gliclazide, Glisoxepide, Glibenclamide, Glipizide, Glibornuride, Glimepiride, Gliquidone, Glyclopyrimide, Tolazamide, Tolbutamide, Chlorpropamide, Metahexamide, Carbutamide, Acetohexamide and combinations thereof, or wherein the sulphonamide is selected from Sulfamethoxazole, Sulfisomidine, Sulfacetamide, Sulfadoxine, Dichlorphenamide (DCP), and Dorzolamide.

23. Improved synergistic composition according to claim 3, said composition capable of ameliorating a side-effect or condition, in a subject treated with the sulfonylurea and/or the derivative and/or the metabolite thereof, and/or the sulfonamide and/or the derivative and/or the metabolite thereof, or the combination thereof, wherein the side-effect or condition arises or is exacerbated as a result of treatment with the sulfonylurea and/or the derivative and/or the metabolite thereof, and/or the sulfonamide and/or the derivative and/or the metabolite thereof, or the combination thereof, optionally wherein the side-effect is selected from hypoglycemia, weight gain, gastrointestinal disturbance, fatigue, and satiety; or optionally wherein the condition is associated with diabetes and the condition is selected from heart and blood vessel disease, nerve damage, kidney damage, eye damage, foot damage, skin and mouth conditions, low bone mineral density and Alzheimer's disease.

24. Method of ameliorating a side-effect or condition, in a subject treated with a sulfonylurea and/or a derivative and/or a metabolite thereof, and/or a sulfonamide and/or a derivative and/or a metabolite thereof, or a combination thereof, wherein the side-effect or condition arises or is exacerbated as a result of treatment with the sulfonylurea and/or the derivative and/or the metabolite thereof, and/or the sulfonamide and/or the derivative and/or the metabolite thereof, or the combination thereof, said method comprising the administration to the subject requiring such treatment comprising inulin having a DP below about 25, in an amount and for a time sufficient to prevent or ameliorate the side effect or condition, optionally wherein the side-effect is selected from hypoglycemia, weight gain, gastrointestinal disturbance, fatigue, and; or optionally wherein the condition is associated with diabetes and the condition is selected from heart and blood vessel disease, nerve damage, kidney damage, eye damage, foot damage, skin and mouth conditions, low bone mineral density and Alzheimer's disease.

25. The method according to claim 24, wherein inulin is administered to the subject simultaneously or sequentially, in any order, with the sulfonylurea and/or the derivative and/or the metabolite thereof, and/or the sulfonamide and/or the derivative and/or the metabolite thereof, or the combination thereof.

26. Improved synergistic composition according to claim 7, wherein unit dosage form comprises from about 100 mg to about 5000 mg of inulin, and wherein the unit dosage form further comprises from about 1mg to about 500 mg of a sulfonylurea, and/or a derivative and/or a metabolite thereof, and/or a sulfonamide and/or a derivative and/or a metabolite thereof, or a combination thereof.

27. Improved synergistic composition according to claim 7, wherein unit dosage form comprises from about 500 mg to about 2000 mg of inulin, and wherein the unit dosage form further comprises from about 1 mg to about 15 mg of a sulfonylurea, and/or a derivative and/or a metabolite thereof, and/or a sulfonamide and/or a derivative and/or a metabolite thereof, or a combination thereof.

28. The method according to claim 20 wherein the inulin is administered to the subject in the amount from about 100 mg to about 5000 mg; or wherein the inulin is administered to the subject in the amount from about 500 mg to about 2000 mg.

29. The method according to claim 21 wherein the sulfonylurea, and/or a sulfonamide and/or derivatives and/or metabolites thereof, or combinations thereof is administered to the subject in the amount from about 1 mg to about 500 mg; or wherein the sulfonylurea, and/or a sulfonamide and/or derivatives and/or metabolites thereof, or combinations thereof is administered to the subject in the amount from about 1 mg to about 15 mg.

* * * * *